(12) United States Patent (10) Patent No.: US 9,370,511 B2
Lammert et al. (45) Date of Patent: Jun. 21, 2016

(54) MORPHINAN-DERIVATIVES FOR TREATING DIABETES AND RELATED DISORDERS

(76) Inventors: Eckhard Lammert, Düsseldorf (DE); Jan Marquard, Düsseldorf (DE); Thomas Meissner, Mettmann (DE)

( * ) Notice: Subject to any disclaimer, the term of this patent is extended or adjusted under 35 U.S.C. 154(b) by 0 days.

(21) Appl. No.: 14/241,131

(22) PCT Filed: Aug. 22, 2012

(86) PCT No.: PCT/EP2012/003552
§ 371 (c)(1),
(2), (4) Date: Oct. 2, 2014

(87) PCT Pub. No.: WO2013/029762
PCT Pub. Date: Mar. 7, 2013

(65) Prior Publication Data
US 2015/0087669 A1 Mar. 26, 2015

(30) Foreign Application Priority Data

Aug. 26, 2011 (EP) .................................... 11006980
Dec. 21, 2011 (EP) .................................... 11010129

(51) Int. Cl.
*A61K 31/44* (2006.01)
*A61K 31/485* (2006.01)
*A61K 31/155* (2006.01)

(52) U.S. Cl.
CPC ............. *A61K 31/485* (2013.01); *A61K 31/155* (2013.01)

(58) Field of Classification Search
CPC .................................................. A61K 31/485
USPC ....................................................... 514/289
See application file for complete search history.

(56) References Cited

FOREIGN PATENT DOCUMENTS

| WO | 02/13759 | A2 | 2/2002 |
| WO | WO 0213759 | * | 2/2002 |
| WO | 2006/094674 | A1 | 9/2006 |
| WO | WO 2006094674 | * | 9/2006 |
| WO | 2008/137474 | A1 | 11/2008 |

OTHER PUBLICATIONS

Goldstein, Proce. Natl. Acd. Sci. USA 1990, 87, 1629-1632.*
Hadcock NPL filed Mar. 27, 2014 Cite No. 2).*
Nelson et al. Neurology May 1997;48(5):1212-8.*
Marquard et al. Nature Medicine vol. 21 No. Apr. 4, 2015, 363-372.*
Wolheim et al Nature Medicine vol. 21 No. Apr. 4, 2015, 310-311.*
Tanaka et al. The Annals of Pharmacotherapy n. Jan. 2011, vol. 4, e1.*
Konrad, et al., "Insulin-dependent diabetes mellitus induced by the antitussive agent dextromethorphan.", Diabetologia, vol. 43, No. 2, Feb. 1, 2000, pp. 261-262.
Hadcock, et al., "Role of opiates and their receptors in the regulation of food intake and body weight", Drug discovery today: Therapeutic strategies, elsevier, vol. 2, No. 2, Jul. 1, 2005, pp. 171-175.
Goldstein et al., "Dextrorphan binds to opioid receptors in guinea-pig brain membranes and is an antagonist at opioid receptors in myenteric plexus", Proc Natl Acad. Sci., Jan. 1, 1990, pp. 1629-1632.
Matsuo., "Effect of dextromethorphan on hyperinsulinemia and growth disturbance in monosodium L-glumate induced obese mice", Kyoto-Furitsu Ika Daigaku Zasshi, 1996, vol. 11874, No. 105, 3, pp. 357-367.
Pittinger et al., "The effect of nalorphine, levallorphan and analogues of levallorphan upon the hyperglycemic response of dogs to levorphan." J. Pharmacology and Exp. Therapeutics; Aug. 1995, vol. 114, No. 4, pp. 439-444.
Lowy et al., "Stereoselective effects of opiate agonists and antagonists on ingestive behavior in rats", Pharmacology biochemistry and behavior, Oct. 1, 1981, Elsevier, US, vol. 15, No. 4, pp. 591-596.
PCT Written Opinion of the International Searching Authority of International Application No. PCT/EP2012/003552 dated Aug. 22, 2012.
Monyer et al., "Morphinans attenuate cortical neuronal injury induced by glucose deprivation in vitro", Brain Research, 446 (1988) 144-148.
Nelson et al., "High-dose oral dextromethorphan versus placebo in painful diabetic neuropathy and postherpetic neuralgia"., Neurology, 1997:48:1212-1218.
Tecoma et al., "Traumatic Neuronal Injury In Vitro is Attenuated by NMDA Antagonists", Neuron, Jun. 1989, vol. 2, 1541-1545.
Barclay et al., "Levorphanol effective in neuropathic pain," N. Engl.J. Med. 2003:248:1223-1232, Abstract only.

* cited by examiner

*Primary Examiner* — Nizal Chandrakumar
(74) *Attorney, Agent, or Firm* — Scott Houtteman; Kile Park Reed & Houtteman PLLC

(57) ABSTRACT

The invention relates to a morphinan-derivative that targets NMDA receptors on pancreatic islets and has the general formula (I)

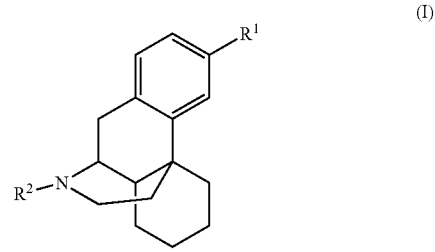

wherein
$R^1$ is selected from —OH, —$CO_2$H, —$R^0$, —$OR^0$, —OC(=O)$R^0$, —OC(=O)$OR^0$ or —OC(=O)NH$R^0$; and $R^2$ is selected from —H, —$R^0$, —C(=O)$R^0$, —C(=O)$OR^0$, —C(=O)NH$R^0$ or —C(=NH)—NH—C(=NH)—NH$_2$; wherein $R^0$ is in each case independently selected from —$C_1$-$C_6$-alkyl, -aryl, -heteroaryl, —$C_1$-$C_6$-alkyl-aryl or —$C_1$-$C_6$-alkyl-heteroaryl, in each case independently unsubstituted or substituted;
or its physiologically acceptable salt and/or stereoisomer, including mixtures thereof in all ratios, for use in the treatment of a disease or condition, where the disease or condition is insulin-dependent diabetes mellitus, non-insulin-dependent diabetes mellitus, obesity, and/or diabetic nephropathy.

7 Claims, 12 Drawing Sheets

Figure 9
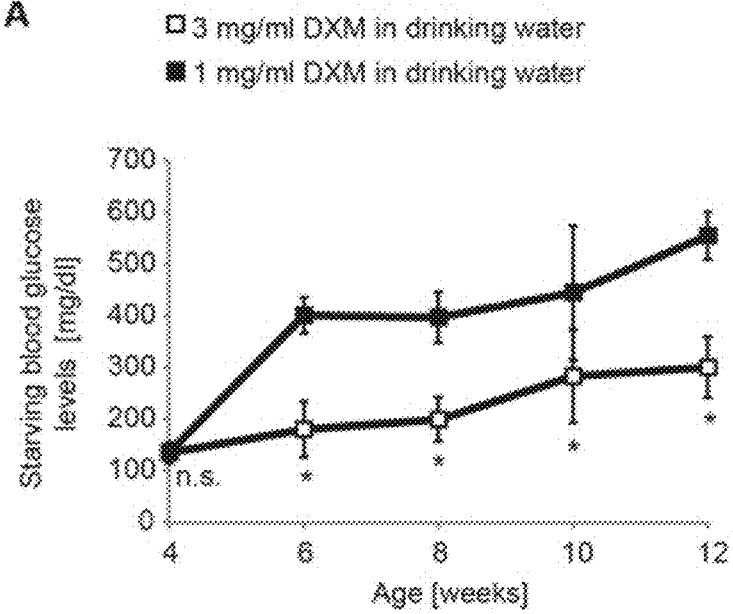
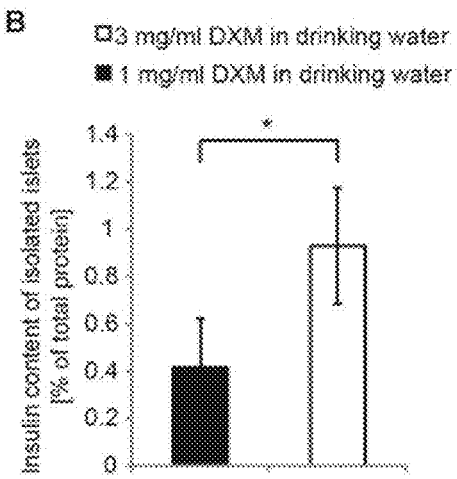 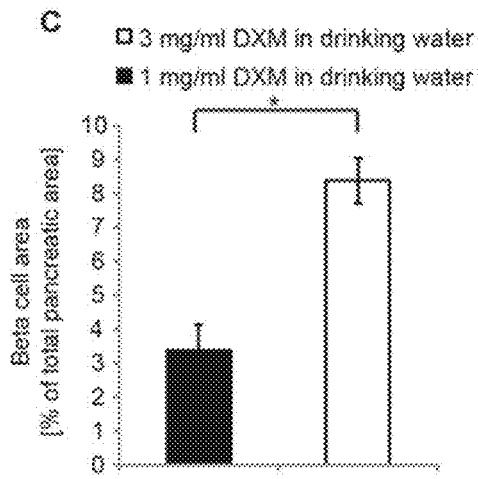

MORPHINAN-DERIVATIVES FOR TREATING DIABETES AND RELATED DISORDERS

FIELD OF INVENTION

The invention relates to morphinan-derivatives, pharmaceutical compositions containing such morphinan-derivatives and the use of those morphinan-derivatives and/or compositions for treating diseases and conditions in man and other mammals, either alone or in combination with other anti-diabetic treatments, where the disease or condition is insulin-dependent diabetes mellitus, non-insulin-dependent diabetes mellitus, obesity, neuropathy and/or nephropathy, preferably diabetic nephropathy.

BACKGROUND OF THE INVENTION

Diabetes is the most frequent metabolic disease. In 2010 about 285 million people suffered from diabetes worldwide, with a steadily increasing incidence. It has been estimated that in 2030 about 439 million people will suffer from diabetes worldwide. In Germany, about 6 to 7 million people live with diabetes, 90-95% with type 2 diabetes.

Diabetes mellitus is the most expensive chronic disorder, causing costs of about 25 billion Euros in Germany in 2005. The costs have been steadily increasing and were about 40 billion Euros in 2010. More than ¾ of these costs are associated with the treatment of subsequent disorders; chronic hyperglycemia is deemed to be an independent risk factor for vessel complications and might cause retinopathy, myocardial infarct, apoplexia, neuropathy, nephropathy and even renal failure.

Type 2 diabetes is characterized by a defective insulin release in response to glucose, a defective response to insulin by liver, fat and muscle cells, enhanced glucose blood levels, reduced glucose tolerance, enhanced insulin blood levels, enhanced triglycerides and enhanced fat tissue. Inflammatory cytokines are enhanced in diabetes patients. Overweight is one of main key predictors for diabetes type 2 and a good correlation between obesity and abnormal glucose tolerance is described in several studies. A defective insulin release in response to glucose is a major defect in type 2 diabetes.

Therapy of type 2 diabetes aims at reducing the chronically increased glucose level in the blood as well as improving the existing insulin resistance.

Oral antidiabetic drugs that have been currently available so far are problematic and not satisfactory in every respect.

Glucose levels in blood can be effectively decreased by administration of sulfonylureas and insulin. However, such treatment is associated with a high risk of hypoglycemia, having the consequence of ambulant or stationary treatment, particularly in the elderly. Three or more severe hypoglycemias in patients suffering from type 2 diabetes have been found to substantially increase the risk of developing dementia. In addition, sulfonylureas are associated with an increased risk of mortality, in particular when combined with metformin.

DDP-4 inhibitors have a low risk of hypoglycemia, but merely lead to a slight improvement of the HbA1c-value compared to metformin. Further, there is no long-term evidence as to tolerability, mortality and diabetes complications.

Most long-term experiences are available for metformin, an extensively administered antidiabetic drug. It is particularly effective in overweight diabetics and reduces diabetes complications and mortality by about 30%. However, monotherapy is typically effective only in the beginning of the treatment; in view of deteriorating function of beta cells and decrease of insulin segregation a second oral antidiabetic drug, typically sulfonylureas, or insulin, must usually be administered in the course of long term treatment.

Currently available diabetes medications cannot suppress or at least decelerate progressive destruction of beta cells.

Morphinan-derivatives have been known as medicaments for many years. The compounds have shown only minor adverse events upon long term administration and thus, are generally well tolerated.

D. Konrad et al., Diabetologia 2000, 43(2):261-2 report that high-dose dextromethorphan in children with severe bacterial meningitis unexpectedly caused the development of type I (insulin dependent) diabetes mellitus as serious adverse event. The study reports on two children suffering from severe bacterial meningitis who developed an insulin dependent diabetes mellitus while taking 36 mg kg$^{-1}$ day$^{-1}$ dextromethorphan. It has to be mentioned that these patients received intensive care treatment besides glucocorticoids, which are known to induce a diabetic metabolic state. Importantly, the diabetes completely disappeared after the treatment for bacterial meningitis was stopped. Since these two bacterial meningitis patients do not represent the population of type I or type II diabetic patients, the reference has no relevance as to the usefulness of dextromethorphan in the treatment of diabetes.

K. A. Nelson et al., Neurology, 48(5), 1997, 1212-8 discloses that dextromethorphan is effective in treating painful diabetic neuropathy.

H. Monyer et al., Brain Research, 446(1), 1988, 144-8 discloses that morphinans attenuate neuronal injury induced by glucose deprivation.

E. S. Tecome at al., Neuron, 2(6), 1989, 1541-5 reports that dextrorphan is a neuroprotective agent useful against neuronal injury.

WO 2008/137474 discloses compounds that are said to be useful for treating diabetic neuropathy, neurological diseases, brain injury and neuropathic pain.

J. R. Hadcock et al., Drug Discovery Today: Therapeutic Strategies, 2(2), 2005, 171-5 discloses that butorphanol and other opioid agonists are orexigenic in humans, while opioid antagonists are antiorexigenic.

A. Goldstein et al., Proc. Natl. Acad. Sci. USA 1990, 1629-32 discloses dextrorphane as a $\mu$ receptor antagonist.

L. Barclay, 2003, XP55012440, Internet discloses levorphanol, the enantiomer of dextrorphan, is a $\mu$ receptor agonist useful in treating neuropathic pain.

WO 02/13759 discloses $\mu$ agonists, such as levorphanol, for use in the treatment of diabetes type 2.

There is a demand for alternative treatments of diabetes and related disorders that overcome the drawback of the prior art. It is therefore an object of the invention to provide medicaments that are useful for the treatment of diseases or conditions selected from insulin-dependent diabetes mellitus, non-insulin-dependent diabetes mellitus, obesity, neuropathy and/or nephropathy that have advantages compared to the prior art.

This object has been achieved by the subject-matter of the patent claims.

SUMMARY OF THE INVENTION

The invention relates to a morphinan-derivative that targets NMDA receptors on pancreatic islets and has the general formula (I)

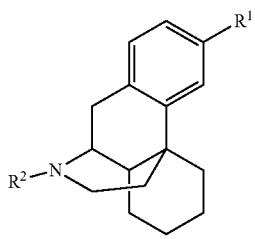

(I)

wherein
R¹ is selected from —OH, —CO₂H, —R⁰, —OR⁰, —OC(=O)R⁰, —OC(=O)OR⁰ or —OC(=O)NHR⁰; and
R² is selected from —H, —R⁰, —C(=O)R⁰, —C(=O)OR⁰, —C(=O)NHR⁰, or —C(=NH)—NH—C(=NH)—NH₂;
wherein
R⁰ is in each case independently selected from —C₁-C₆-alkyl, -aryl, -heteroaryl, —C₁-C₆-alkyl-aryl or —C₁-C₆-alkyl-heteroaryl, in each case independently unsubstituted or substituted;

or its physiologically acceptable salt and/or stereoisomer, including mixtures thereof in all ratios, for use in the treatment of a disease or condition, where the disease or condition is insulin-dependent diabetes mellitus, non-insulin-dependent diabetes mellitus, obesity, neuropathy and/or nephropathy, preferably diabetic nephropathy.

In a preferred embodiment, R¹ is —CO₂H or R¹ is —R⁰, wherein R⁰ is —C₁-C₆-alkyl substituted with one or more groups —CO₂H, such as —CH₂—CO₂H, —CH₂CH₂—CO₂H, —CH(CH₃)—CO₂H, —CH(CO₂H)₂, —CH₂CH₂CH₂—CO₂H, and the like. Particularly preferably R¹ is —CO₂H, —CH₂—CO₂H or —CH(CH₃)—CO₂H.

Several morphinan-derivatives are known as pharmacologically active substances (cf. B. Y. Wong et al., Neuroscience Letters 1988, 85 (2): 261-6; J. Church et al., Canadian Journal of Physiology and Pharmacology, 1989, 67 (6): 561-7; I. R. Kamel et al., Journal of Neurosurgical Anesthesiology, 2008, 20 (4): 241-8).

It has now been surprisingly found that the morphinan-derivatives according to the invention increase the secretion of insulin only at elevated glucose concentrations. If the glucose concentration is within the physiologically normal range, however, insulin secretion is not induced.

Thus, the morphinan-derivatives according to the invention surprisingly do not risk the development of hypoglycemia with its long-term complications, including dementia and death. This is an essential advantage of the invention over the prior art.

Further, it has been known that certain substances that are known to have a similar mechanism of action as morphinan-derivatives exhibit neuroprotective activity (G. C. Palmer, Curr Drug Targets 2001, 2:241-71). As beta cells have much in common with neurons (I. Konstantinova et al., Cell 2007, 129:359-70; D. Eberhard et al., Curr Opin Genet Dev. 2009, 19:469-75), there is indication that morphinan-derivatives also protect beta cells and thus, can significantly slow down the progression of type 2 diabetes.

It has been reported that opioid receptor antagonists might be useful for the treatment of obesity. This is not relevant for the subject invention, since the morphinan-derivatives according to the invention exhibit neither pronounced opioid receptor agonist nor opioid receptor antagonist activity. Instead, the morphinan-derivatives according to the invention are useful for treating obesity due to their NMDA receptor inhibition and sigma-1 receptor activation. Importantly, even though sigma-1 receptors were once considered to be opioid receptors in the past, they are nowadays not classified with the opioid receptors any longer. This is because they are different in both function and gene sequence (see e.g. Cobos et al., Neuropharmacol., 2008, 6(4), 344). In particular, a pharmacological study on rats concludes that the effects of dextrorphan are not mediated by opioid receptors (see Pechnick et al., J. Pharmacol. Exp. Ther. 2004, 309(2), 515).

The morphinan-derivatives according to the invention can be administered in form of a monotherapy or alternatively, in combination with metformin, thereby preventing or retarding the subsequently necessary administration of sulfonylureas or insulin.

BRIEF DESCRIPTION OF THE DRAWINGS

FIG. 9 shows the results of long-term treatment of db/db mice (an animal model for human type 2 diabetes mellitus) with a low, ineffective dose of 1 mg/ml dextromethorphan and an effective dose of 3 mg/ml dextromethorphan in drinking water. Treatment of db/db mice with the effective dose of dextromethorphan for 8 weeks significantly and continuously results in lower blood glucose levels or better blood glucose control (A). Moreover, the insulin content of islets from db/db mice treated for 8 weeks with the effective dose contained significantly more insulin (B), and the beta cell area was significantly larger, when compared to db/db mice treated with the low dose of dextromethorphan (C).

DETAILED DESCRIPTION OF THE INVENTION

Figure 1:
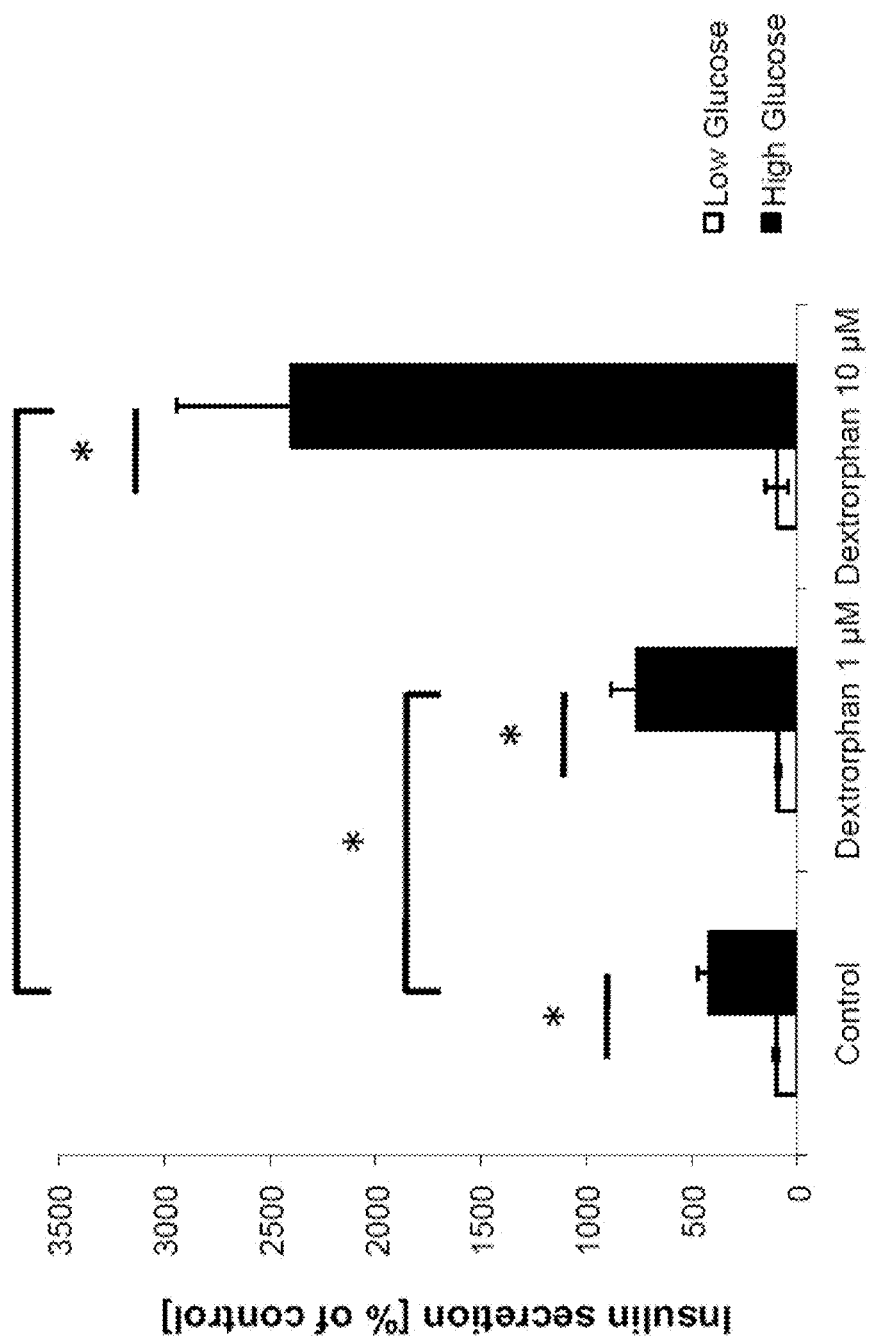
FIG. 1 shows insulin secretion from mouse pancreatic islets in the presence and absence of dextrorphan. Low Glucose (2.5 mM); High Glucose (25 mM); p<0.05 (Student's t-Test), N=3.

The invention relates to a morphinan-derivative that targets NMDA receptors on pancreatic islets and has the general formula (I)

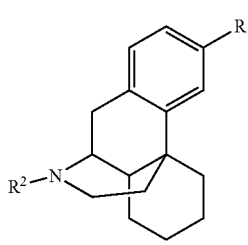

(I)

wherein
$R^1$ is selected from —OH, —$CO_2H$, —$R^0$, —$OR^0$, —OC(=O)$R^0$, —OC(=O)$OR^0$ or —OC(=O)$NHR^0$; and
$R^2$ is selected from —H, —$R^0$, —C(=O)$R^0$, —C(=O)$OR^0$, —C(=O)$NHR^0$ or —C(=NH)—NH—C(=NH)—$NH_2$;
wherein
$R^0$ is in each case independently selected from —$C_1$-$C_6$-alkyl, -aryl, -heteroaryl, —$C_1$-$C_6$-alkyl-aryl or —$C_1$-$C_6$-alkyl-heteroaryl, in each case independently unsubstituted or substituted;
or its physiologically acceptable salt and/or stereoisomer, including mixtures thereof in all ratios, for use in the treatment of a disease or condition, where the disease or condition is insulin-dependent diabetes mellitus, non-insulin-dependent diabetes mellitus, obesity, neuropathy and/or nephropathy, preferably diabetic nephropathy.

In a preferred embodiment, $R^1$ is —OH, —$CH_3$ or —$OCH_3$; and/or $R^2$ is —H or —$CH_3$.

In preferred embodiments, $R^1$ is —$OCH_3$ and $R^2$ is —$OCH_3$; or $R^1$ is —$OCH_3$ and $R^2$ is —$CH_3$; or $R^1$ is —OH and $R^2$ is —$CH_3$; or $R^1$ is —$OCH_3$ and $R^2$ is —H; or $R^1$ is —OH and $R^2$ is —$CH_3$; or $R^1$ is —$CH_3$ and $R^2$ is —$CH_3$; or $R^1$ is —$CO_2H$ and $R^2$ is —$CH_3$, or $R^1$ is —$CH_2$—$CO_2H$ and $R^2$ is —$CH_3$, or $R^1$ is —CH($CH_3$)—$CO_2H$ and $R^2$ is —$CH_3$; or $R^1$ is —CH($CH_3$)—$CO_2H$ and $R^2$ is —$CH_3$; or $R^1$ is —$OCH_3$ and $R^2$ is —C(=NH)—NH—C(N=H)—$NH_2$.

In a preferred embodiment, $R^1$ is —$C_nH_{2n}$—$CO_2H$ where n is an integer of from 0 to 12, preferably 0, 1, 2 or 3; whereas $R^2$ is preferably —H or —$CH_3$. Preferably, $R^1$ is —$CO_2H$, —$CH_2$—$CO_2H$, —$CH_2CH_2$—$CO_2H$, —CH($CH_3$)—$CO_2H$, —CH($CO_2H$)$_2$, —$CH_2CH_2CH_2$—$CO_2H$, and the like. Particularly preferably $R^1$ is —$CO_2H$, —$CH_2$—$CO_2H$ or —CH($CH_3$)—$CO_2H$.

In another preferred embodiment, $R^2$ is —C(=NH)—NH—C(N=H)—$NH_2$; whereas $R^1$ is preferably —H or —$CH_3$.

In a particularly preferred embodiment, the morphinan-derivative according to the invention has a stereochemistry according to general formula (II):

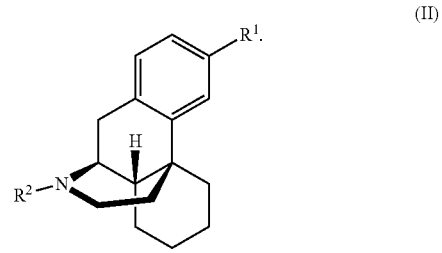

(II)

Preferred representatives are depicted here below:

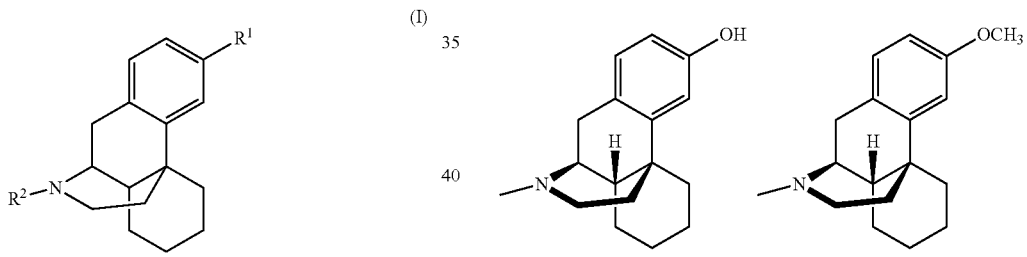

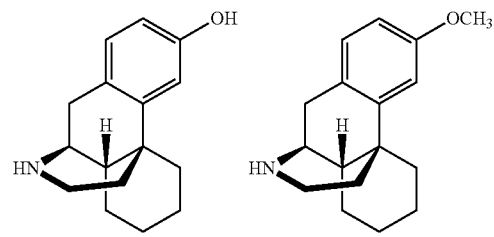

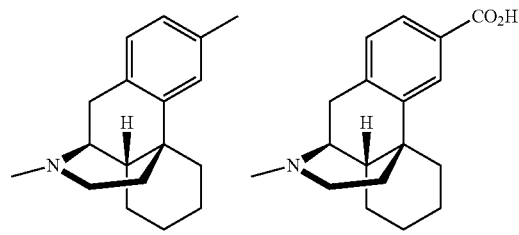

-continued

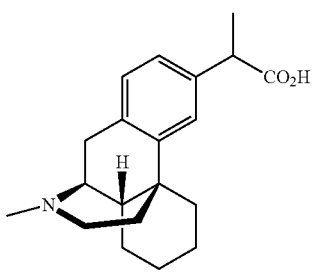

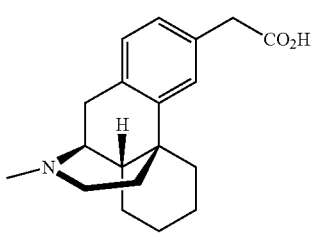

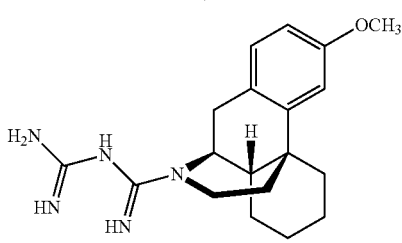

The above compounds usually rotate polarized light in (+)-direction (dextrorotatory) and the chiral centers usually have S-configuration according to CIP-nomenclature, although this may of course change depending upon the substituents.

The above compounds are commercially available or can be synthesized by standard derivatization of commercially available building blocks. In particular, commercially available are Dextromethorphan (i.e., (+)-3-methoxy-17-methyl-(9α,13α,14α)-morphinan, wherein $R^1$=—$OCH_3$, $R^2$=—$CH_3$); Dextrorphan (i.e., (+)-17-methyl-9a,13a,14a-morphinan-3-ol, wherein $R^1$=—OH, $R^2$=—$CH_3$); 3-Hydroxymorphinan (i.e., (+)-9a,13a,14a-morphinan-3-ol, wherein $R^1$=—OH, $R^2$=—H); and 3-Methoxymorphinan (i.e., (+)-3-methoxy-(9α,13α,14α)-morphinan, wherein $R^1$=—$OCH_3$, $R^2$=—H). By standard derivatization, derivatives of these morphinans can be obtained such as carboxylated Dextrorphan (i.e., (+)-3-carboxy-17-methyl-9a,13a, 14a-morphinan, wherein $R^1$=—COOH, $R^2$=—$CH_3$); Dextrorphan-propionic acid (i.e., (+)-17-methyl-9a, 13a, 14a-morphinan-3-propionate, wherein $R^1$=—CH—($CH_3$)—COOH, $R^2$=—$CH_3$); Dextrorphan-acetate (i.e., (+)-17-methyl-9a,13a,14a-morphinan-3-acetate, wherein $R^1$=—$CH_2$—COOH, $R^2$=—$CH_3$); or Metformin-Dextromethorphan (i.e., (+)-3-methoxy-17-metformin-(9α,13α,14α)-morphinan, wherein $R^1$=—$OCH_3$, $R^2$=Metformin). As far as standard derivatization reactions are concerned it can be referred to e.g. R. Larock, Comprehensive Organic Transformations: A Guide to Functional Group Preparations, Wiley-VCH, New York; and Houben-Weyl Methods of Organic Chemistry, Thieme, Stuttgart.

Thus, particularly preferably, the morphinan-derivative is a (+)-morphinan-derivative selected from the group consisting of (+)-17-methyl-(9a-13a-14a)-morphinan-3-ol (Dextrorphan), (+)-3-methoxy-17-methyl-(9a-13a-14a)-morphinan (Dextromethorphan), (+)-3-hydroxy-(9a-13a-14a)-morphinan, (+)-3-methoxy-(9a-13a-14a)-morphinan, (+)-3,17-dimethyl-(9a-13a-14a)-morphinan (Dimemorfan), and GCC 1290K, a prodrug of 3-hydroxy-(9a-13a-14a)-morphinan, or the physiologically acceptable salt and/or stereoisomer thereof, including mixtures thereof in all ratios.

GCC 1290K, isopropyl-[(9a-13a-14a)-morphinan-3-yloxy]methyl carbonate, is known e.g. from US 2010/0113500 and has the following structure:

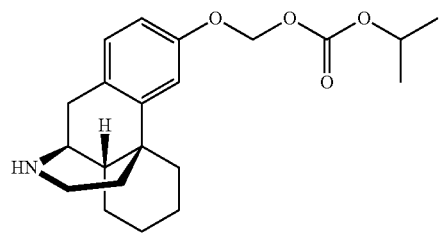

The invention relates to the morphinan-derivatives according to the invention as medicaments and/or medicament active ingredients in the treatment and/or prophylaxis of diseases or conditions selected from insulin-dependent diabetes mellitus, non-insulin-dependent diabetes mellitus, obesity, neuropathy and/or nephropathy, preferably diabetic nephropathy; and to the use of the morphinan-derivatives according to the invention for the preparation of a pharmaceutical composition or pharmaceutical dosage form for the treatment and/or prophylaxis of the said diseases; and also to a method for the treatment of the said diseases which comprises the administration of an effective amount of one or more morphinan-derivatives according to the invention to a subject in need of such an administration.

The invention also relates to morphinan-derivatives, preferably (+)-morphinan-derivatives, according to general formula (II) as such

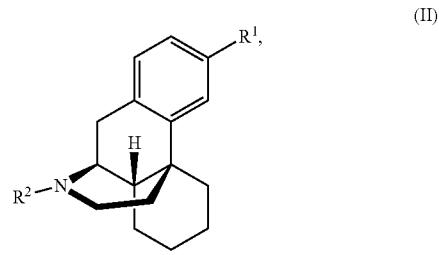

(II)

wherein (i) either $R^1$ is —$C_nH_{2n}$—$CO_2H$ where n is an integer of from 0 to 12, preferably 0, 1, 2 or 3; and $R^2$ is —H or —$R^0$, preferably —H or —$CH_3$;

(ii) or $R^1$ is selected from —OH, —OR⁰, or —OC(=O)R⁰; and $R^2$ is —C(=NH)—NH—C(=NH)—NH$_2$;
   wherein R⁰ is defined as above;
or its physiologically acceptable salt and/or stereoisomer, including mixtures thereof in all ratios.

Preferred representatives of these (+)-morphinan-derivatives according to the invention include, but are not limited to
carboxylated Dextrorphan (i.e., (+)-3-carboxy-17-methyl-9a,13a,14a-morphinan, wherein $R^1$=—COOH, $R^2$=—CH$_3$);
Dextrorphan-propionic acid (i.e., (+)-17-methyl-9a,13a,14a-morphinan-3-propionate, wherein $R^1$=—CH—(CH$_3$)—COOH, $R^2$=—CH$_3$);
Dextrorphan-acetate (i.e., (+)-17-methyl-9a,13a,14a-morphinan-3-acetate, wherein $R^1$=—CH$_2$—COOH, $R^2$=—CH$_3$); and
Metformin-Dextromethorphan (i.e., (+)-3-methoxy-17-metformin-(9α,13α,14α)-morphinan, wherein $R^1$=—OCH$_3$, $R^2$=Metformin):

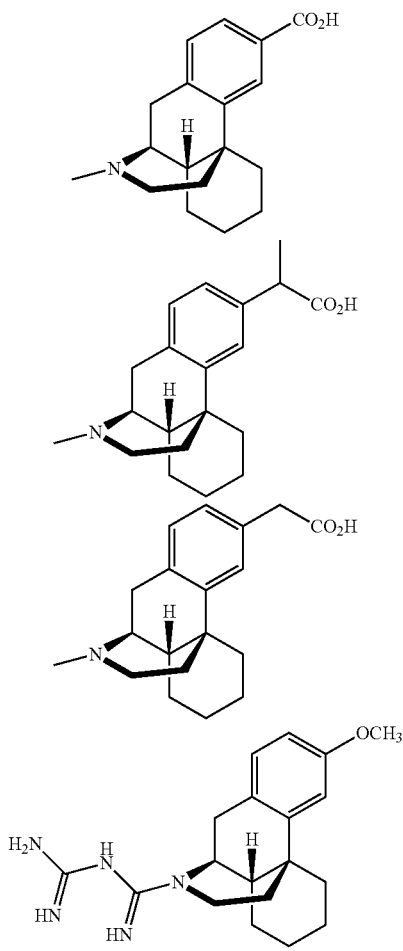

The morphinan-derivatives according to the invention are not only useful for the treatment of insulin-dependent diabetes mellitus, but also for the treatment of non-insulin-dependent diabetes mellitus. This is because patients with non-insulin-dependent diabetes mellitus do also profit from beta-cell-stimulating therapies. As a matter of fact, the World Health Organization (WHO) placed the oral antidiabetic drug glibenclamide in their 17th edition of *Essential Medicine* in category 18.5, *Insulin and other medicines used for diabetes*.

Glibenclamide stimulates insulin secretion from pancreatic islets of non-insulin-dependent diabetic patients, in particular type II diabetics. However, since glibenclamide stimulates basal insulin secretion from pancreatic islets to a large extent, hypoglycemic adverse events are encountered by this drug. In contrast to glibenclamide, however, the morphinan-derivatives according to the invention such as dextrorphan stimulate basal insulin secretion from pancreatic islets to a lesser extent. Thus, the morphinan-derivatives according to the invention likely have lesser hypoglycemic adverse effects compared to glibenclamide.

The morphinan-derivatives according to the invention are useful for treating diabetes mellitus type 2; particularly in overweight patients, when dietary management and exercise alone does not result in adequate glycemic control. The morphinan-derivatives may be used as monotherapy or in combination with other oral antidiabetic agents such as metformin, or with insulin.

The host or patient may belong to any mammal species, for example a primate species, particularly humans; rodents, including mice, rats and hamsters; rabbits; horses, cows, dogs, cats, etc. Animal models are of interest for experimental investigations, where they provide a model for the treatment of a human disease.

The morphinan-derivatives according to the invention also mean the physiologically acceptable derivatives and solvates.

The invention also relates to the stereoisomers and the hydrates and solvates of these morphinan-derivatives. Solvates of the morphinan-derivatives include adductions of inert solvent molecules onto the morphinan-derivatives which form owing to their mutual attractive force. Solvates are, for example, mono- or dihydrates or alcoholates.

The morphinan-derivatives include the physiologically acceptable salts of the morphinan-derivatives according to the invention and also the prodrugs thereof. For example, GCC 1290K is a preferred produg of 3-hydroxy-(9a-13a-14a)-morphinan, wherein the 3-hydroxy group is etherified by a carbonate residue —CH$_2$—O—C(=O)—O—CH(CH$_3$)$_2$ and which is optionally provided in form of the tartrate.

Prodrugs mean morphinan-derivatives which have been modified, with, for example, alkyl or acyl groups, sugars or oligopeptides and which are rapidly cleaved in the organism to form the active morphinan-derivatives according to the invention. These also include biodegradable polymer derivatives of the morphinan-derivatives according to the invention.

The expression "effective amount" means the amount of a medicament or pharmaceutical active ingredient which causes a biological or medical response which is sought or aimed at, for example by a researcher or physician, in a tissue, system, animal or human.

In addition, the expression "therapeutically effective amount" means an amount which, compared with a corresponding subject who has not received this amount, has the following consequence: improved treatment, healing, prevention or elimination of a disease, syndrome, condition, complaint, disorder or prevention of side effects or also the reduction in the progress of a disease, condition, disorder or side effects or also the reduction in the progress of a disease, condition or disorder. The expression "therapeutically effective amount" also encompasses the amounts which are effective for increasing normal physiological function.

The invention also relates to mixtures of the morphinan-derivatives according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

For all radicals, which occur more than once, their meanings are independent of one another.

In the morphinan-derivatives according to general formula (I), $R^0$ is in each case independently selected from $-C_1-C_6$-alkyl, -aryl, -heteroaryl, $-C_1-C_6$-alkyl-aryl or $-C_1-C_6$-alkyl-heteroaryl, in each case independently unsubstituted or substituted. A particularly preferred substituent of $R^0$ is $-CO_2H$, so that preferred representatives of substituted residues $R^0$ include, but are not limited to $-C_1-C_6$-alkyl-$CO_2H$, -aryl-$CO_2H$, -heteroaryl-$CO_2H$, $-C_1-C_6$-alkyl-aryl-$CO_2H$ and $-C_1-C_6$-alkyl-heteroaryl-$CO_2H$. Another particularly preferred substituent of $R^0$ is $-OH$, so that preferred representatives of substituted residues $R^0$ include, but are not limited to $-C_1-C_6$-alkyl-OH, -aryl-OH, -heteroaryl-OH, $-C_1-C_6$-alkyl-aryl-OH and $-C_1-C_6$-alkyl-heteroaryl-OH.

For the purpose of the specification, $-C_1-C_6$-alkyl means alkyl that is unbranched (linear) or branched, and has 1, 2, 3, 4, 5, or 6 C atoms, preferably -methyl, -ethyl, -propyl, -isopropyl, -butyl, -isobutyl, -sec-butyl, -tert-butyl, -pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. Substituted $-C_1-C_6$-alkyl include but are not limited to $-C_1-C_6$-alkyl-$CO_2H$, $-C_1-C_6$-alkyl-F, $-C_1-C_6$-alkyl-Cl, $-C_1-C_6$-alkyl-OH, $-C_1-C_6$-alkyl-O-$C_1-C_6$-alkyl and the like.

For the purpose of the specification, aryl denotes -phenyl, -naphthyl or -biphenyl.

For the purpose of the specification, heteroaryl denotes an aromatic monocyclic group, or a bicyclic group in which at least one of the rings is aromatic, each group containing from 5 to 11 ring members and from 1 to 5 hetero atoms selected from nitrogen, oxygen and sulphur.

For the purpose of the specification, substituents of $-C_1-C_6$-alkyl, -aryl, -heteroaryl, $-C_1-C_6$-alkyl-aryl or $-C_1-C_6$-alkyl-heteroaryl include one or more substituents independently of one another selected from -halogen, $-C_1-C_6$-alkyl, $-C_1-C_6$-alkoxy, hydroxy, mercapto, $-C_1-C_6$-alkylthio, -cyano, -amino (optionally substituted by one or two $-C_1-C_6$-alkyl), -nitro, -carboxy, $-C_1-C_6$-alkoxycarbonyl, -aminocarbonyl (optionally substituted by one or two $-C_1-C_6$-alkyl) or -carbamoyl, or $-O-C(=O)-O-C_1-C_6$-alkyl, enantiomers and diastereoisomers thereof, and addition salts thereof with a pharmaceutically acceptable acid or base. Polar substituents such as -carboxy are particularly preferred. The carboxy groups may be protonated or may be present as salts with suitable counter cations such as sodium, potassium, ammonium and the like.

The morphinan-derivatives have chiral centers and can therefore occur in various stereoisomeric forms. The general formula (I) encompasses all these forms.

The morphinan-derivatives according to the invention and also the starting materials for their preparation are prepared by methods known per se, as described in the literature (for example in the standard works, such as Houben-Weyl, Methoden der organischen Chemie [Methods of Organic Chemistry], Georg-Thieme-Verlag, Stuttgart), under reaction conditions which are known and suitable for the said reactions. Use can also be made here of variants known per se, which are not mentioned here in greater detail.

If desired, the starting materials can also be formed in situ so that they are not isolated from the reaction mixture, but instead are immediately converted further into the morphinan-derivatives according to the invention.

The starting compounds are generally known. If they are novel, however, they can be prepared by methods known per se.

The morphinan-derivatives according to the invention can be used in their final non-salt form. On the other hand, the invention also encompasses the use of these morphinan-derivatives in the form of their pharmaceutically acceptable salts, which can be derived from various organic and inorganic acids and bases by procedures known in the art. Pharmaceutically acceptable salt forms of the morphinan-derivatives are for the most part prepared by conventional methods. If the morphinan-derivative contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the morphinan-derivatives are likewise included.

In the case of certain morphinan-derivatives, acid-addition salts can be formed by treating the morphinan-derivatives with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the morphinan-derivatives include, but are not limited to acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, and phthalate.

Furthermore, the base salts of the morphinan-derivatives according to the invention include, but are not limited to aluminium, ammonium, calcium, copper, iron(III), iron(II), lithium, magnesium, manganese(III), manganese(II), potassium, sodium and zinc salts, but this is not intended to represent a restriction. Salts of the morphinan-derivatives which are derived from pharmaceutically acceptable organic non-toxic bases include, but are not limited to salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine).

The morphinan-derivatives of the invention typically contain basic nitrogen-containing groups that can be quaternized using agents such as —$C_1$-$C_4$-alkyl halides, for example -methyl, -ethyl, -isopropyl and -tert-butyl, -chloride, -bromide and -iodide; -di($C_1$-$C_4$)alkyl sulfates, for example -dimethyl, -diethyl and -diamyl sulfate; —($C_{10}$-$C_{18}$)alkyl halides, for example -decyl, -dodecyl, -lauryl, -myristyl -and stearyl chloride, bromide and iodide; and -aryl($C_1C_4$)alkyl halides, for example -benzyl chloride and -phenethyl bromide. Both water- and oil-soluble morphinan-derivatives according to the invention can be prepared using such salts.

The above-mentioned pharmaceutical salts which are preferred include, but are not limited to acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine.

The acid-addition salts of basic morphinan-derivatives are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

The pharmaceutically acceptable base-addition salts of the morphinan-derivatives are preferably formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic morphinan-derivatives according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a morphinan-derivative according to the invention contains more than one group which is capable of forming pharmaceutically acceptable salts of this type, the invention also encompasses multiple salts. Typical multiple salt forms include, but are not limited to bitartrate, diacetate, difumarate, dimeglumine, diphosphate, disodium and trihydrochloride.

Accordingly, the expression "pharmaceutically acceptable salt" for the purpose of the specification means an active ingredient which comprises a morphinan-derivative in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The morphinan-derivatives according to the invention are chiral owing to their molecular structure and may accordingly occur in various enantiomeric forms. They therefore exist in racemic or in optically active form. Since the pharmaceutical activity of the racemates or stereoisomers of the morphinan-derivatives according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the morphinan-derivatives and/or physiologically acceptable salts thereof for the preparation of medicament (pharmaceutical composition), in particular by non-chemical methods. They can be converted into a suitable dosage form here together with at least one solid, liquid and/or semi-liquid excipient or adjuvant and, if desired, in combination with one or more further active ingredients.

The invention furthermore relates to medicaments comprising at least one morphinan-derivative according to the invention and/or physiologically acceptable salts and stereoisomers thereof, including mixtures thereof in all ratios, and optionally excipients and/or adjuvants.

Pharmaceutical formulations can be administered in the form of pharmaceutical dosage forms which comprise a predetermined amount of active ingredient per pharmaceutical dosage forms. Such a unit can comprise, for example, 1 mg to 2 g, preferably 50 mg to 1.5 g, particularly preferably 100 mg to 1 g, of a morphinan-derivative according to the invention, depending on the disease condition treated, the method of administration and the age, weight and condition of the patient, or pharmaceutical formulations can be administered in the form of pharmaceutical dosage forms which comprise a predetermined amount of morphinan-derivative per pharmaceutical dosage forms. Preferred pharmaceutical dosage forms formulations are those which comprise a daily dose or part-dose, as indicated above, or a corresponding fraction thereof of an active ingredient. Furthermore, pharmaceutical formulations of this type can be prepared using a process which is generally known in the pharmaceutical art. For comparison, the anti-diabetic drug metformin is currently administered in units of 500 mg to 1 g.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the morphinan-derivative can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubilizer, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets.

The morphinan-derivatives according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different pharmaceutical dosage forms.

Oral liquids, such as, for example, solution, syrups and elixirs, can be prepared in the form of pharmaceutical dosage forms so that a given quantity comprises a pre specified amount of the morphinan-derivatives. Syrups can be prepared by dissolving the morphinan-derivatives in an aqueous solution with a suitable flavour, while elixirs are prepared using a non-toxic alcoholic vehicle. Suspensions can be formulated by dispersion of the morphinan-derivatives in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The pharmaceutical dosage forms formulations for oral administration can, if desired, be encapsulated in microcapsules. The formulation can also be prepared in such a way that the release is extended or retarded, such as, for example, by coating or embedding of particulate material in polymers, wax and the like.

The morphinan-derivatives according to the invention and salts, solvates and derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The morphinan-derivatives according to the invention and the salts, solvates and derivatives thereof can also be delivered using monoclonal antibodies as individual carriers to which the morphinan-derivatives are coupled. The morphinan-derivatives can also be coupled to soluble polymers as targeted medicament carriers. Such polymers may encompass polyvinylpyrrolidone, pyran copolymer, polyhydroxypropyl-methacrylamidophenol, polyhydroxyethylaspartamidophenol or polyethylene oxide polylysine, substituted by palmitoyl radicals. The morphinan-derivatives may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the morphinan-derivatives can be delivered from the plaster by iontophoresis.

Pharmaceutical compositions adapted for topical administration can be formulated as ointments, creams, suspensions, lotions, powders, solutions, pastes, gels, sprays, aerosols or oils.

Pharmaceutical formulations adapted for topical application in the mouth encompass lozenges, pastilles and mouth-washes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass solutions of the morphinan-derivatives in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

In addition to the above particularly mentioned constituents, the formulations may also comprise other agents usual in the art with respect to the particular type of formulation; thus, for example, formulations which are suitable for oral administration may comprise flavours.

A therapeutically effective amount of a morphinan-derivative of the invention depends on a number of factors, including, for example, the age and weight of the human or animal, the precise disease condition which requires treatment, and its severity, the nature of the formulation and the method of administration, and is ultimately determined by the treating physician or veterinarian. However, an effective amount of a morphinan-derivative according to the invention is generally in the range from 0.1 to 100 mg/kg of body weight of the recipient (mammal) per day and particularly typically in the range from 4 to 40 mg/kg of body weight per day. Thus, the actual amount per day for an adult mammal weighing 70 kg is usually between 500 mg and 3 g, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the morphinan-derivative according to the invention per se. It can be assumed that similar doses are suitable for the treatment of other conditions mentioned above. For comparison, the daily dose of metformin used in type 2 diabetic patients is similarly 500 mg to 3 g.

In a particularly preferred embodiment, the morphinan-derivative according to the invention is administered once daily, or twice daily, or thrice daily, or four times daily, the individually administered dose per administration being within the range of 60±15 mg, or 90±15 mg, or 100±15 mg, or 120±15 mg, or 150±15 mg, or 180±15 mg, or 210±15 mg, or 240±15 mg, or 270±15 mg, or 300±15 mg, or 310±15 mg, or 340±15 mg, or 370±15 mg, or 400±15 mg, or 410±15 mg, or 440±15 mg, or 470±15 mg, or 500±15 mg, or 750±15 mg, or 1,000±15 mg.

In a preferred embodiment, particularly when the morphinan-derivative according to the invention is intended for administration over an extended period of time such as several months or years, it is preferred to initiate administration at a comparatively low daily dose and to consecutively, preferably steadily increase the daily dose over a titration period until the desired maximum daily dose has been reached (dose titration). Once the maximum daily dose has been reached, the titration period is terminated and continuous administration proceeds which may also include a subsequent reduction of the daily dose, if desired.

In the following embodiments, the daily dose of the morphinan-derivative is preferably administered on each day, independently of one another, all at once (once daily, sid), divided in two portions (twice daily, bid), divided in three portions (thrice daily), or divided in four portions (four times daily).

In a preferred embodiment, the titration regimen is biphasic, i.e. includes the administration of two different daily doses $d_1$ and $d_2$, wherein daily dose $d_1$ is administered during a first administration interval $a_1$, preferably on every day, and daily dose $d_2$ is administered during a second administration interval $a_2$, preferably on every day, which second administration interval $a_2$ follows the first administration interval $a_1$, and wherein daily dose $d_1$<daily dose $d_2$. Preferably, daily dose $d_2$ is the maximum daily dose to be finally administered, and daily dose $d_1$ is within the range of from 10 to 90 wt.-% of daily dose $d_2$, more preferably 20 to 80 wt.-%, still more preferably 30 to 70 wt.-%, and most preferably 40 to 60 wt.-% of daily dose $d_2$. Preferably, the first administration interval $a_1$ comprises at least 2 days, more preferably at least 4 days, still more preferably at least 7 days, yet more preferably at least 14 days, even more preferably at least 21 days, most preferably at least 28 days, and in particular at least 2 months. Preferably, the second administration interval $a_2$ comprises at least 2 days, more preferably at least 4 days, still more preferably at least 7 days, yet more preferably at least 14 days, even more preferably at least 21 days, most preferably at least 28 days, and in particular at least 2 months. Thus, according to this embodiment, the titration period comprises the first administration interval $a_1$.

In another preferred embodiment, the titration regimen is triphasic, i.e. includes the administration of three different daily doses $d_1$, $d_2$ and $d_3$, wherein daily dose $d_1$ is administered during a first administration interval $a_1$, preferably on every day, daily dose $d_2$ is administered during a second administration interval $a_2$, preferably on every day, which second administration interval $a_2$ follows the first administration interval $a_1$, and daily dose $d_3$ is administered during a third administration interval $a_3$, preferably on every day, which third administration interval $a_3$ follows the second administration interval $a_2$, and wherein daily dose $d_1$<daily dose $d_2$<daily dose $d_3$. Preferably, daily dose $d_3$ is the maximum daily dose to be finally administered; and daily dose $d_1$ is within the range of from 5 to 55 wt.-% of daily dose $d_3$, more preferably 10 to 50 wt.-%, still more preferably 15 to 45 wt.-%, and most preferably 20 to 40 wt.-% of daily dose $d_3$; and daily dose $d_2$ is within the range of from 45 to 95 wt.-% of daily dose $d_3$, more preferably 50 to 90 wt.-%, still more preferably 55 to 85 wt.-%, and most preferably 60 to 80 wt.-% of daily dose $d_3$. Preferably, the first administration interval $a_1$ comprises at least 2 days, more preferably at least 4 days, still more preferably at least 7 days, yet more preferably at least 14 days, even more preferably at least 21 days, most preferably at least 28 days, and in particular at least 2 months. Preferably, the second administration interval $a_2$ comprises at least 2 days, more preferably at least 4 days, still more preferably at least 7 days, yet more preferably at least 14 days, even more preferably at least 21 days, most preferably at least 28 days, and in particular at least 2 months. Preferably, the third administration interval $a_3$ comprises at least 2 days, more preferably at least 4 days, still more preferably at least 7 days, yet more preferably at least 14 days, even more preferably at least 21 days, most preferably at least 28 days, and in particular at least 2 months. Thus, according to this embodiment, the titration period comprises the first administration interval $a_1$ as well as the second administration interval $a_2$.

In a preferred embodiment, the titration regimen is multiphasic, i.e. includes the administration of a multitude of different daily doses $d_1$, $d_2$, $d_3$, ... $d_n$, wherein daily dose $d_1$ is administered during a first administration interval $a_1$, preferably on every day, daily dose $d_2$ is administered during a second administration interval $a_2$, preferably on every day, which second administration interval $a_2$ follows the first administration interval $a_1$, daily dose $d_3$ is administered during a third administration interval $a_3$, preferably on every day, which third administration interval $a_3$ follows the second administration interval $a_2$, and so on, until daily dose $d_n$ is administered during a final administration interval $a_n$ of the titration period, preferably on every day, and wherein daily dose $d_1$<daily dose $d_2$<daily dose $d_3$< ... <$d_n$. For example, daily dose $d_1$ may amount to 120 mg of the morphinan-derivative. Daily dose $d_1$ may be administered all at once (once daily, sid), divided in two portions each amounting to 60 mg (twice daily, bid), divided in three portions each amounting to 40 mg (thrice daily), or divided in four portions each amounting to 30 mg (four times daily). During the titration phase, the daily dose $d_1$ may be increased up to a maximum daily dose $d_n$ of e.g. 960 mg. For example, during a titration phase of four weeks the daily dose may be increased by 30 mg to 60 mg, e.g. every three days, unless the patient reports complete therapeutic effect, side effects that interfere with daily activities, or unless the maximum daily dose $d_n$ is reached. Thus, the further increase of the daily dose during the titration phase depends on the perception of the patient. In the following administration interval (maintenance phase), the highest well-tolerated daily dose can be maintained at a constant level.

The invention furthermore relates to medicaments comprising at least one morphinan-derivative according to the invention and/or physiologically acceptable salts and stereoisomers thereof, including mixtures thereof in all ratios, and at least one further medicament active ingredient.

The invention also relates to a set (kit) comprising separate packs of (a) an effective amount of a morphinan-derivative according to the invention and/or physiologically acceptable salts and stereoisomers thereof, including mixtures thereof in all ratios; and (b) an effective amount of a further medicament active ingredient.

The set comprises suitable containers, such as boxes, individual bottles, bags or ampoules. The set may, for example, comprise separate ampoules, each containing an effective amount of a compound according to the invention and/or physiologically acceptable salts and stereoisomers thereof, including mixtures thereof in all ratios, and an effective amount of a further active ingredient in dissolved or lyophilised form. Preferably, said further active ingredient is metformin or a physiologically acceptable salt thereof.

The morphinan-derivatives are suitable as pharmaceutical active ingredients for mammals, in particular for humans, in the treatment of diabetes type 1, diabetes type 2, obesity, neuropathy and/or nephropathy, preferably diabetic nephropathy.

The invention thus relates to the use of morphinan-derivatives and to physiologically acceptable derivatives, solvates and stereoisomers, including mixtures thereof in all ratios, for the preparation of a medicament for the treatment of diabetes type 1, diabetes type 2, obesity, neuropathy and/or nephropathy, preferably diabetic nephropathy.

The morphinan-derivatives of the invention can be used as prophylactics or therapeutic agents for treating diseases or disorders mediated by deficient levels of GLP-1 activity or which can be treated by activating TGR5 including, but not limited to, diabetes mellitus, impaired glucose tolerance, IFG (impaired fasting glucose) and IFG (impaired fasting glycemia), as well as other diseases and disorders such as those discussed below. Furthermore, the morphinan-derivatives of the invention can be also used to prevent the progression of the borderline type, impaired glucose tolerance, IFG (impaired fasting glucose) or IFG (impaired fasting glycemia) to diabetes mellitus.

The morphinan-derivatives of the invention can be also used as prophylactics or therapeutic agents of diabetic complications such as, but not limited to, neuropathy, nephropathy, preferably diabetic nephropathy, retinopathy, cataract, macroangiopathy, osteopenia, diabetic hyperosmolar coma), infectious diseases (e.g., respiratory infection, urinary tract infection, gastrointestinal tract infection, dermal soft tissue infection, lower limb infection etc.), diabetic gangrene, xerostomia, decreased sense of hearing, cerebrovascular disease, peripheral circulatory disturbance, etc.

The morphinan-derivatives of the invention can be also used as prophylactics or therapeutic agents in the treatment of diseases and disorders such as, but not limited to, obesity, metabolic syndrome (syndrome X), hyperinsulinemia, hypoinsulinemia, hyperinsulinemia-induced sensory disorder, hypoinsulinemia-induced sensory disorder, dyslipoproteinemia (abnormal lipoproteins in the blood) including diabetic dyslipidemia, hyperlipidemia, hyperlipoproteinemia (excess of lipoproteins in the blood) including type I, II-a (hypercholesterolemia), II-b, III, IV (hypertriglyceridemia) and V (hypertriglyceridemia), low HDL levels, high LDL levels, atherosclerosis and its sequelae, vascular restenosis, neurodegenerative disease, depression, CNS disorders, liver steatosis, osteoporosis, hypertension, renal diseases (e.g., diabetic nephropathy, glomerular nephritis, glomeruloscierosis, nephrotic syndrome, hypertensive nephrosclerosis, terminal renal disorder etc.), myocardiac infarction, angina pectoris, and cerebrovascular disease (e.g., cerebral infarction, cerebral apoplexy).

The morphinan-derivatives of the invention can be also used as prophylactics or therapeutic agents in the treatment of diseases and disorders such as, but not limited to, osteoporosis, fatty liver, hypertension, insulin resistant syndrome, inflammatory diseases (e.g., chronic rheumatoid arthritis, spondylitis deformans, osteoarthritis, lumbago, gout, postoperative or traumatic inflammation, remission of swelling, neuralgia, pharyngolaryngitis, cystitis, hepatitis (including non-alcoholic steatohepatitis), pneumonia, inflammatory colitis, ulcerative colitis), pancreatitis, visceral obesity syndrome, cachexia (e.g., carcinomatous eachexia, tuberculous cachexia, diabetic cachexia, hemopathic cachexia, endocrinopathic cachexia, infectious cachexia, cachexia induced by acquired immunodeficiency syndrome), polycystic ovary syndrome, muscular dystrophy, tumor (e.g., leukemia, breast cancer, prostate cancer, skin cancer etc.), irritable bowel syndrome, acute or chronic diarrhea, spondylitis deformans, osteoarthritis, remission of swelling, neuralgia, pharyngolaryngitis, cystitis, SIDS, and the like.

The morphinan-derivatives of the invention can be used in combination with one or more additional drugs such as described below. The dose of the second drug can be appropriately selected based on a clinically employed dose. The proportion of the morphinan-derivatives and the second drug can be appropriately determined according to the administration subject, the administration route, the target disease, the clinical condition, the combination, and other factors. In cases where the administration subject is a human, for instance, the second drug may be used in an amount of 0.01 to 100 parts by weight per part by weight of the morphinan-derivatives.

The second compound of the pharmaceutical combination formulation or dosing regimen preferably has complementary activities to the morphinan-derivative such that they do not adversely affect each other. Such drugs are suitably present in combination in amounts that are effective for the purpose intended. Accordingly, another aspect of the invention provides a composition comprising a morphinan-derivative according to the invention, or a solvate, metabolite, or pharmaceutically acceptable salt or prodrug thereof, in combination with a second drug, such as described herein.

The morphinan-derivative and the additional pharmaceutically active agent(s) may be administered together in a unitary pharmaceutical composition or separately and, when administered separately this may occur simultaneously or sequentially in any order. Such sequential administration may be close in time or remote in time. The amounts of the morphinan-derivative and the second agent(s) and the relative timings of administration will be selected in order to achieve the desired combined therapeutic effect.

The combination therapy may provide "synergy" and prove "synergistic", i.e., the effect achieved when the active ingredients used together is greater than the sum of the effects that results from using the compounds separately. A synergistic effect may be attained when the active ingredients are (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

The morphinan-derivatives of the invention can be used, for example in combination with additional drug(s) such as a therapeutic agent for diabetes mellitus, and/or a therapeutic agent for diabetic complications, as defined above.

Examples of known therapeutic agents for diabetes mellitus which can be used in combination with a morphinan-derivative include insulin preparations (e.g., animal insulin preparations extracted from the bovine or swine pancreas; human insulin preparations synthesized by a genetic engineering technique using *Escherichia coli* or a yeast), a fragment of insulin or derivatives thereof (e.g., INS-i), agents for improving insulin sensitivity (e.g., pioglitazone hydrochloride, troglitazone, rosiglitazone or its maleate, GI-262570, JTT-50 1, MCC-555, YM-440, KRP-297, CS-Oil, FK-614), alpha-glucosidase inhibitors (e.g., voglibose, acarbose, miglitol, emiglitate), biguanides (e.g., phenformin, metformin, buformin), insulin secretagogues [sulfonylureas (e.g., tolbutamide, glibenclamide, gliclazide, chiorpropamide, tolazamide, acetohexamide, glyclopyramide, glimepiride, glipizide, glybuzole), repaglinide, nateglinide, mitiglinide or its calcium salt hydrate, GLP-1J, dipeptidylpeptidase IV inhibitors (e.g., NVP-DPP-278, PT-100), beta-3 agonists (e.g., CL-3 16243, SR-58611-A, UL-TG-307, SB-226552, AJ-9677, BMS-196085, AZ-40140 etc.), amylin agonists (e.g., pramlintide), phosphotyrosine phosphatase inhibitors (e.g., vanadic acid), gluconeogenesis inhibitors (e.g., glycogen phosphorylase inhibitors, glucose-6-phosphatase inhibitors, glucagon antagonists), SGLT (sodium-glucose cotransporter) inhibitors (e.g., T-1095), and the like.

Examples of known therapeutic agents for diabetic complications include aldose reductase inhibitors (e.g., tolrestat, epairestat, zenarestat, zopobestat, minairestat, fidarestat (SNK-860), CT-i 12), neurotrophic factors (e.g., NGF, NT-3, BDNF), neurotrophic factor production secretion promoters, PKC inhibitors (e.g., LY-333531), AGE inhibitors (e.g., ALT946, pimagedine, pyratoxathine, N-phenacylthiazolium bromide (ALT766), EXO-226), active oxygen scavengers (e.g., thioctic acid), and cerebral vasodilators (e.g., tiapuride, mexiletine).

The morphinan-derivatives of the invention can also be used, for example in combination with antihyperlipidemic agents. Epidemiological evidence has firmly established hyperlipidemia as a primary risk factor in causing cardiovascular disease (CVD) due to atherosclerosis. In recent years, emphasis has been placed on lowering plasma cholesterol levels, and low density lipoprotein cholesterol in particular, as an essential step in prevention of CVD.

Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance. Examples of antihyperlipidemic agents include statin compounds which are cholesterol synthesis inhibitors (e.g., cerivastatin, pravastatin, simvastatin, lovastatin, atorvastatin, fluvastatin, itavastatin or their salts, etc.), squalene synthase inhibitors or fibrate compounds (e.g., bezafibrate, clofibrate, simfibrate, clinofibrate) having a triglyceride lowering action and the like.

The morphinan-derivatives of the invention can also be used, for example in combination with hypotensive agents. Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries, while sodium retention increases blood volume. Thus, the lowering of insulin levels in hyperinsulinemics can prevent abnormal vascular growth and renal sodium retention caused by high insulin levels and thereby alleviates hypertension. Examples of hypotensive agents include angiotensin converting enzyme, inhibitors (e.g., captopril, enalapril, delapril), angiotensin II antagonists (e.g., candesartan cilexetil, losartan, eprosartan, valsantan, termisartan, irbesartan, tasosartan), calcium antagonists (e.g., manidipine, nifedipine, nicardipine, amlodipine, efonidipine), and clonidine.

The morphinan-derivatives of the invention can be used in combination with antiobesity agents. The term "obesity" implies an excess of adipose tissue. Obesity is a well-known risk factor for the development of many very common diseases such as diabetes, atherosclerosis, and hypertension. To some extent appetite is controlled by discrete areas in the hypothalamus: a feeding centre in the ventrolateral nucleus of the hypothalamus (VLH) and a satiety centre in the ventromedial hypothalamus (VMH). The cerebral cortex receives positive signals from the feeding center that stimulate eating, and the satiety center modulates this process by sending inhibitory impulses to the feeding center. Several regulatory processes may influence these hypothalamic centers. The satiety center may be activated by the increases in plasma glucose and/or insulin that follow a meal. Examples of anti-obesity agents include antiobesity drugs acting on the central nervous system (e.g., dexfenfluramine, fenfluramine, phentermine, sibutramine, anfepramon, dexamphetamine, mazindol, phenylpropanolamine, clobenzorex), pancreatic lipase inhibitors (e.g. orlistat), beta-3 agonists (e.g., CL-3 16243, SR-5861 1-A, UL-TG-307, SB-226552, AJ-9677, BMS-196085, AZ-40140), anorectic peptides (e.g., leptin, CNTF (Ciliary Neurotrophic Factor) and cholecystokinin agonists (e.g. lintitript, FPL-1 5849).

EXAMPLES

The following examples further illustrate the invention but are not to be construed as limiting its scope.

Example 1

Mouse pancreatic islets were treated with a low, non-stimulatory glucose concentration (2.5 mM) or a high, stimulatory glucose concentration (25 mM) in the absence or presence of 1 µM or 10 µM dextrorphan. Insulin secretion was determined as percent of 2 mM glucose control, and values are expressed as means+/−SD (N=3). The asterisks (*) indicate p values smaller than 0.05 in Student's t-tests.

FIG. 1 shows insulin secretion from mouse pancreatic islets in the presence and absence of dextrorphan. Low Glucose (2.5 mM); High Glucose (25 mM); $p<0.05$ (Student's t-Test), N=3.

As can be seen, insulin secretion is selectively increased at a high rather than low glucose concentration.

Example 2

Mouse pancreatic islets were treated with a low, non-stimulatory glucose concentration (2.5 mM) or a high, stimulatory glucose concentration (25 mM) in the absence or presence of 1 µM or 10 µM compound (dextromethorphan, 3-hydroxy-morphinan and 3-methoxy-morphinan). Insulin secretion was determined as percent of 2 mM glucose control, and values are expressed as means+/−SD (N=3). The asterisks (*) indicate p values smaller than 0.05 in Student's t-tests.

Figure 2:
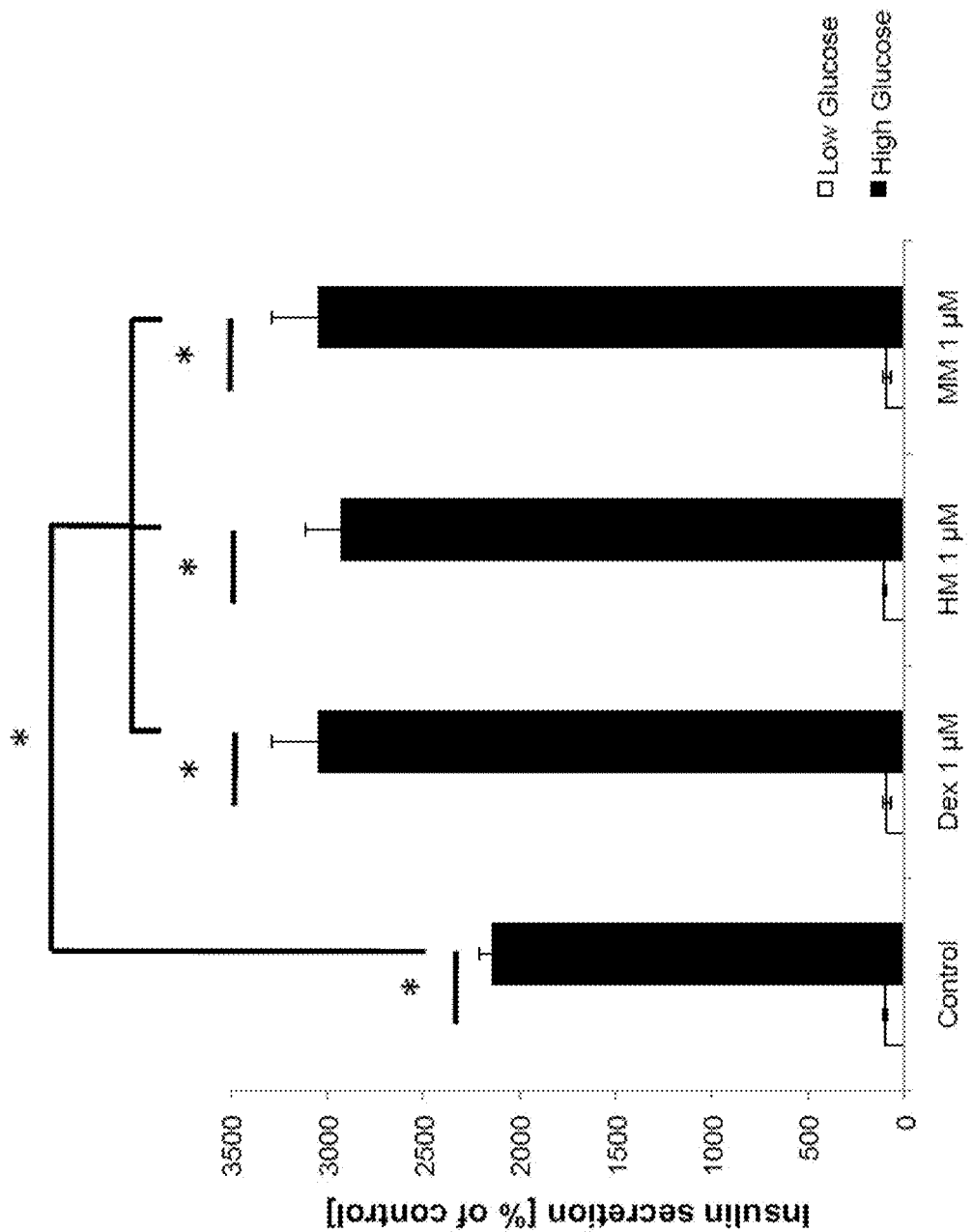
FIG. 2 shows insulin secretion from mouse pancreatic islets in the presence and absence of dextromethorphan (Dex). 3-hydroxy-morphinan (HM) and 3-methoxy-morphinan (MM). Low Glucose (2.5 mM); High Glucose (25 mM); p<0.05 (Student's t-Test), N=3.

FIG. 2 shows insulin secretion from mouse pancreatic islets in the presence and absence of dextromethorphan (Dex), 3-hydroxy-morphinan (HM) and 3-methoxy-morphinan (MM). Low Glucose (2.5 mM); High Glucose (25 mM); $p<0.05$ (Student's t-Test), N=3.

Example 3

Glucose Tolerance Test

Fasted 8 week-old male mice C57BL/6 received an i.p. injection of glucose (2 mg per g (body weight)) at the point of time 0' minutes (control) or glucose together with dextrorphan (40 µg per g (body weight)) (DXO group) at the point of time 0 minutes. Blood glucose levels were determined at the indicated times in FIG. 3. Values are expressed as means±SD (n=6 per group), DXO dextrorphan. P values with Student's t-test.

Example 4

Glucose Tolerance Test

Fasted 8-9 week-old male homozygous BKS.CG-m+/+ Lepr$^{db}$/BomTac (db/db) mice received an i.p. injection of glucose (1 mg per g (body weight)) at the point of time 0' minutes (control) or glucose together with dextrorphan (50 µg per g (body weight)) (DXO group) at the point of time 0 minutes. Blood glucose levels were determined at the indicated times in FIG. 4. Values are expressed as means±SD (n=6 per group). Glucose levels were determined with a glucometer with the measurement range 20-600 mg/dl. All glucose levels above 600 mg/dl were estimated as 600 ml/dg. DXO dextrorphan. P values with Student's t-test.

Figure 3:
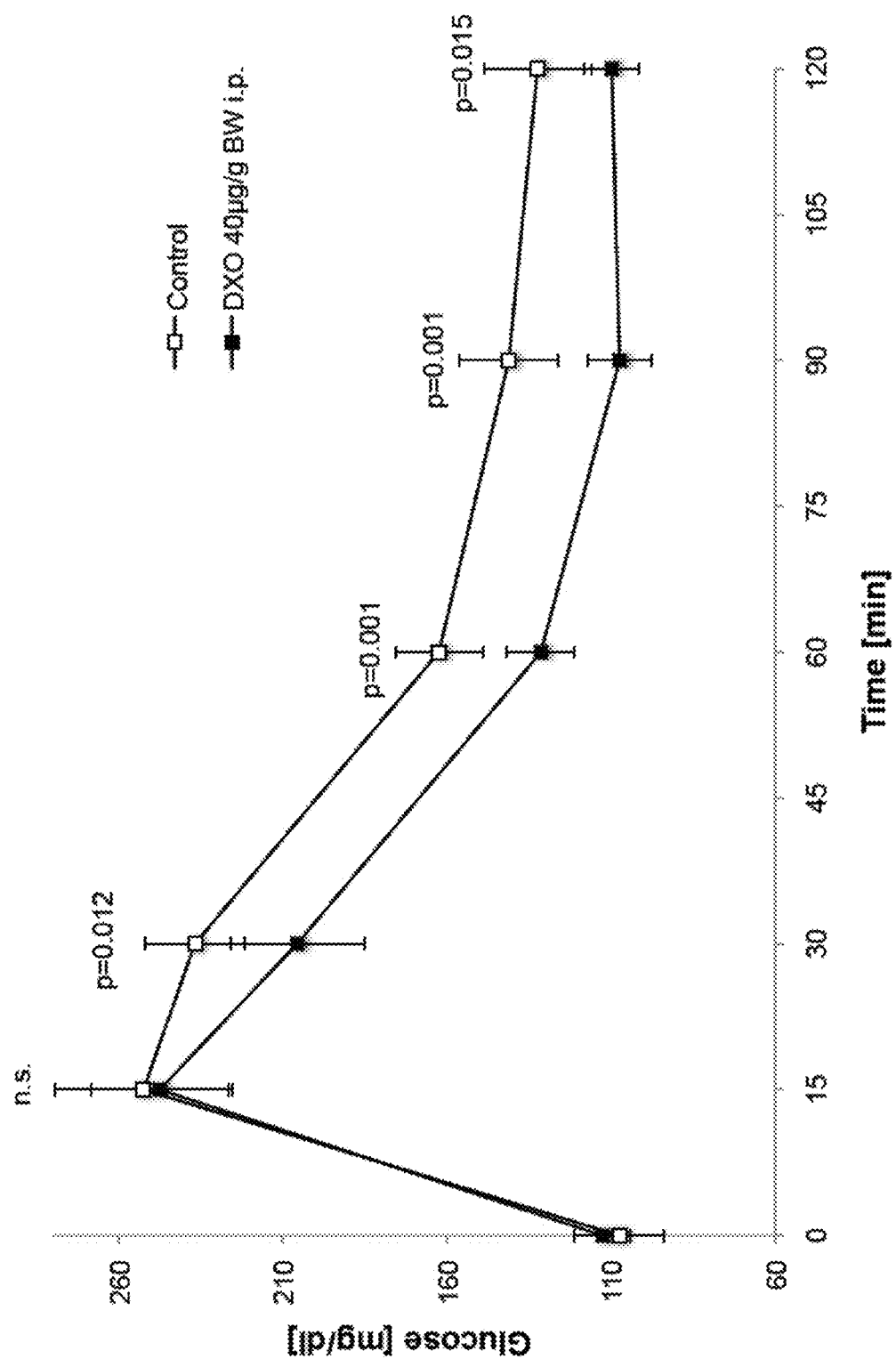
FIGS. 3 and 4 show the results of a glucose tolerance test after administration of dextrorphan in healthy C57BL/6 and type 2 diabetic db/db mice, respectively.
Figure 4:
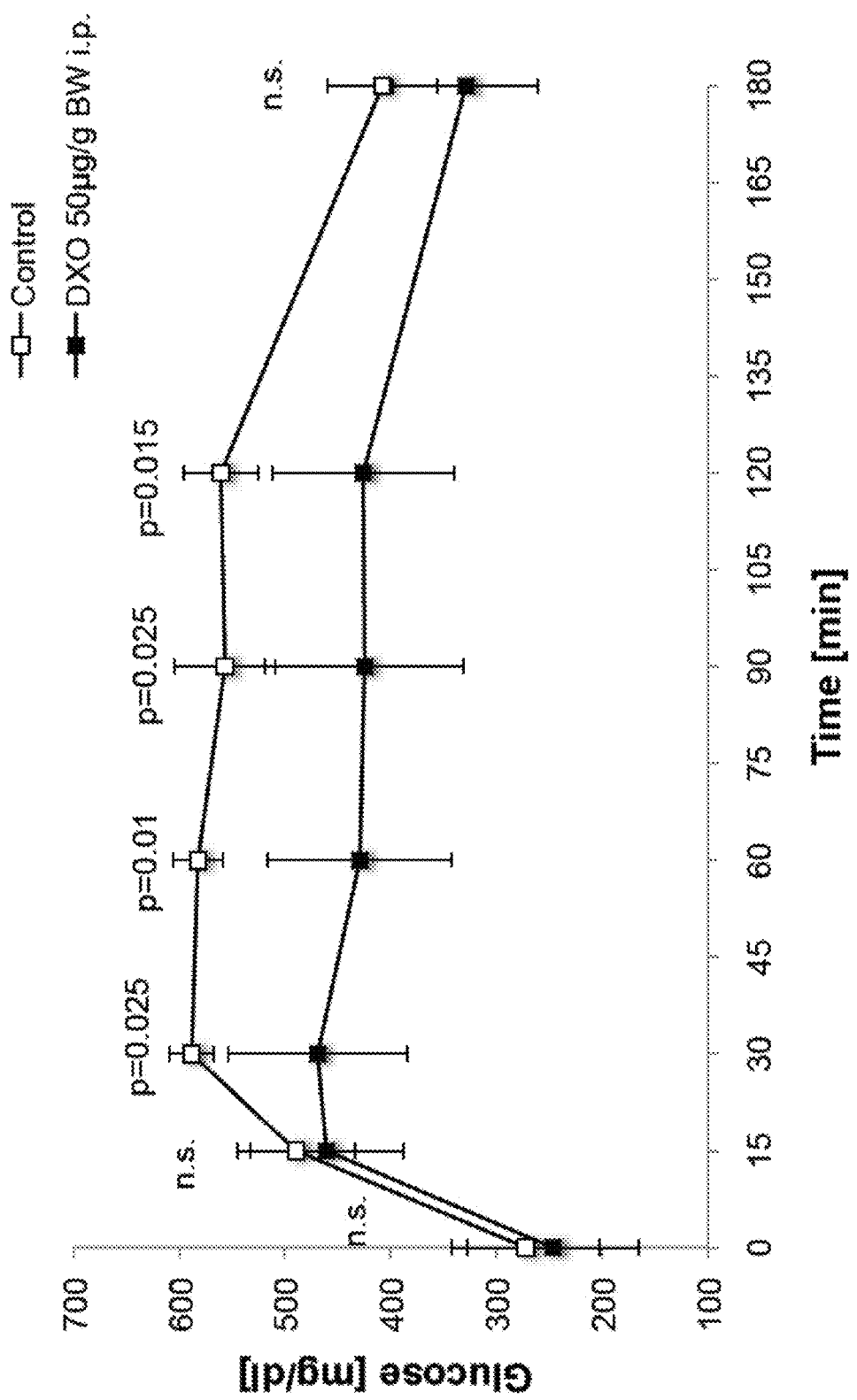

As can be seen, in FIG. 3, non-diabetic C57BL/6 mice, and in FIG. 4, diabetic db/db mice show a significantly improved glucose tolerance upon drug application.

Example 5

Example 1 was repeated but dextrorphan was replaced by dimemorfan.

Figure 5:
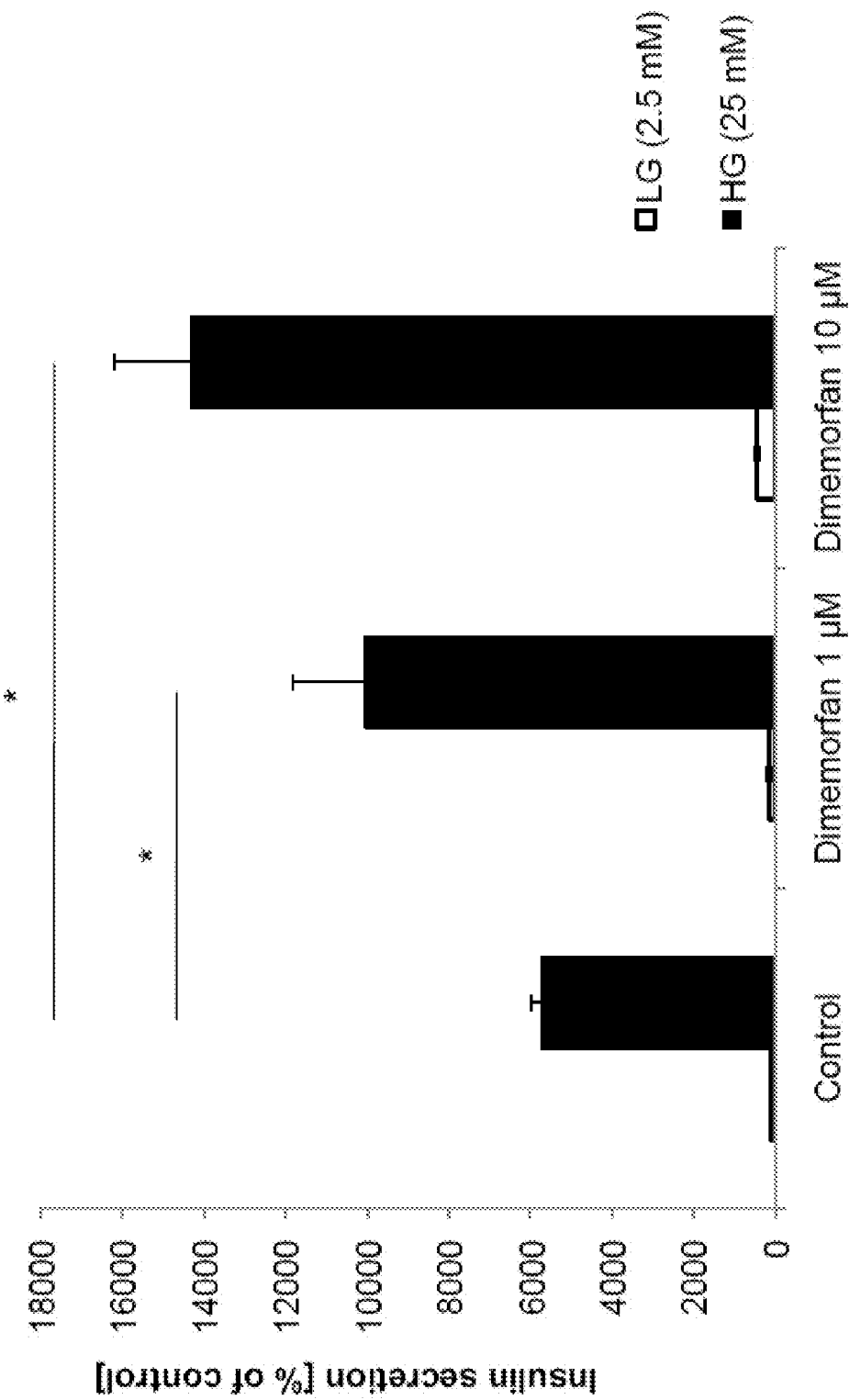
FIG. 5 shows the insulin secretion from mouse pancreatic islets in the absence and presence of dimemorfan 1 μM and 10 μM. Low Glucose (2.5 mM), High Glucose (25 mM).

FIG. 5 shows insulin secretion from mouse pancreatic islets in the presence and absence of dimemorfan 1 and 10 µM. Low Glucose (2.5 mM); High Glucose (25 mM); $p<0.05$ (Student's t-Test), N=5.

Example 6

Example 1 was repeated but the mouse pancreatic islets were replaced by human pancreatic islets.

Figure 6:
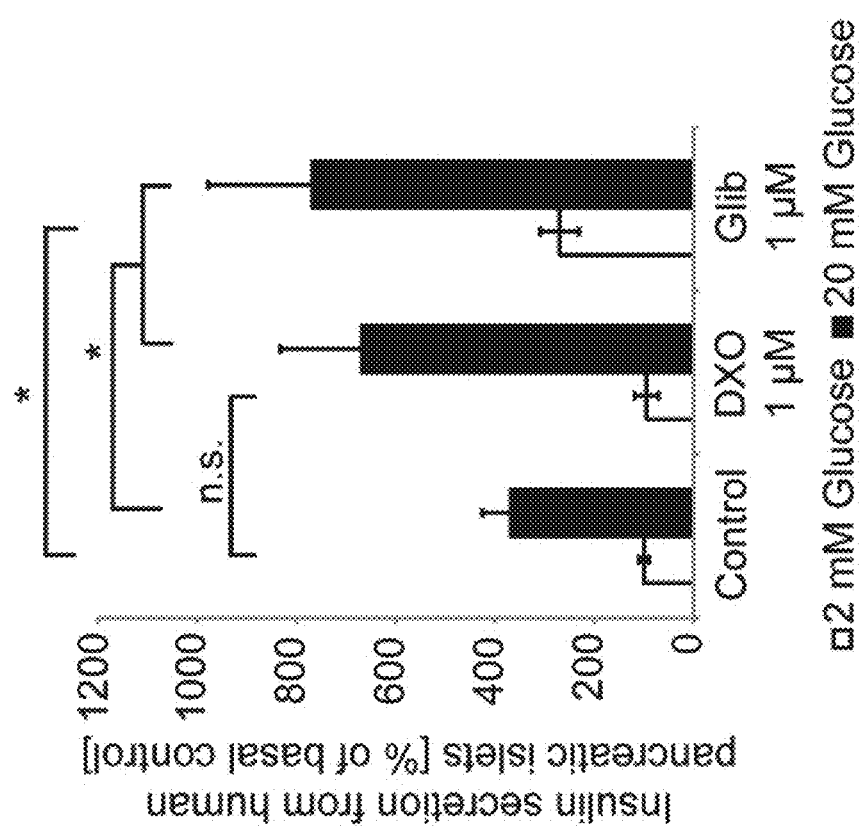
FIG. 6 shows insulin secretion from human pancreatic islets in the presence and absence of 1 μM dextrorphan and 1 μM glibenclamide. Low Glucose (2 mM); High Glucose (20 mM); The asterisks (*) indicate p values smaller than 0.05 in Student's t-tests. The Figure shows that in contrast to glibenclamide, dextrorphan only increases insulin secretion from human pancreatic islets at a high glucose concentration, but not at a low glucose concentration. Increasing insulin secretion at a low glucose concentration is associated with life-threatening hypoglycemia as observed under glibenclamide treatment.

FIG. 6 shows insulin secretion from human pancreatic islets in the presence and absence of 1 µM dextrorphan and 1 µM glibenclamide. Low Glucose (2 mM); High Glucose (20 mM); the asterisks (*) indicate p values smaller than 0.05 in Student's t-tests.

As can be seen in FIG. 6, dextrorphan selectively increases glucose stimulated insulin secretion rather than basal insulin secretion, whereas glibenclamide increases both basal (2 mM glucose) and glucose-stimulated (20 mM glucose) insulin secretion from human pancreatic islets. Thus, dextrorphan is not expected to induce life-threatening hypoglycemia in diabetic patients, as reported for glibenclamide.

Example 7

Example 6 was repeated but dextrorphan was replaced by dimemorphan.

Figure 7:
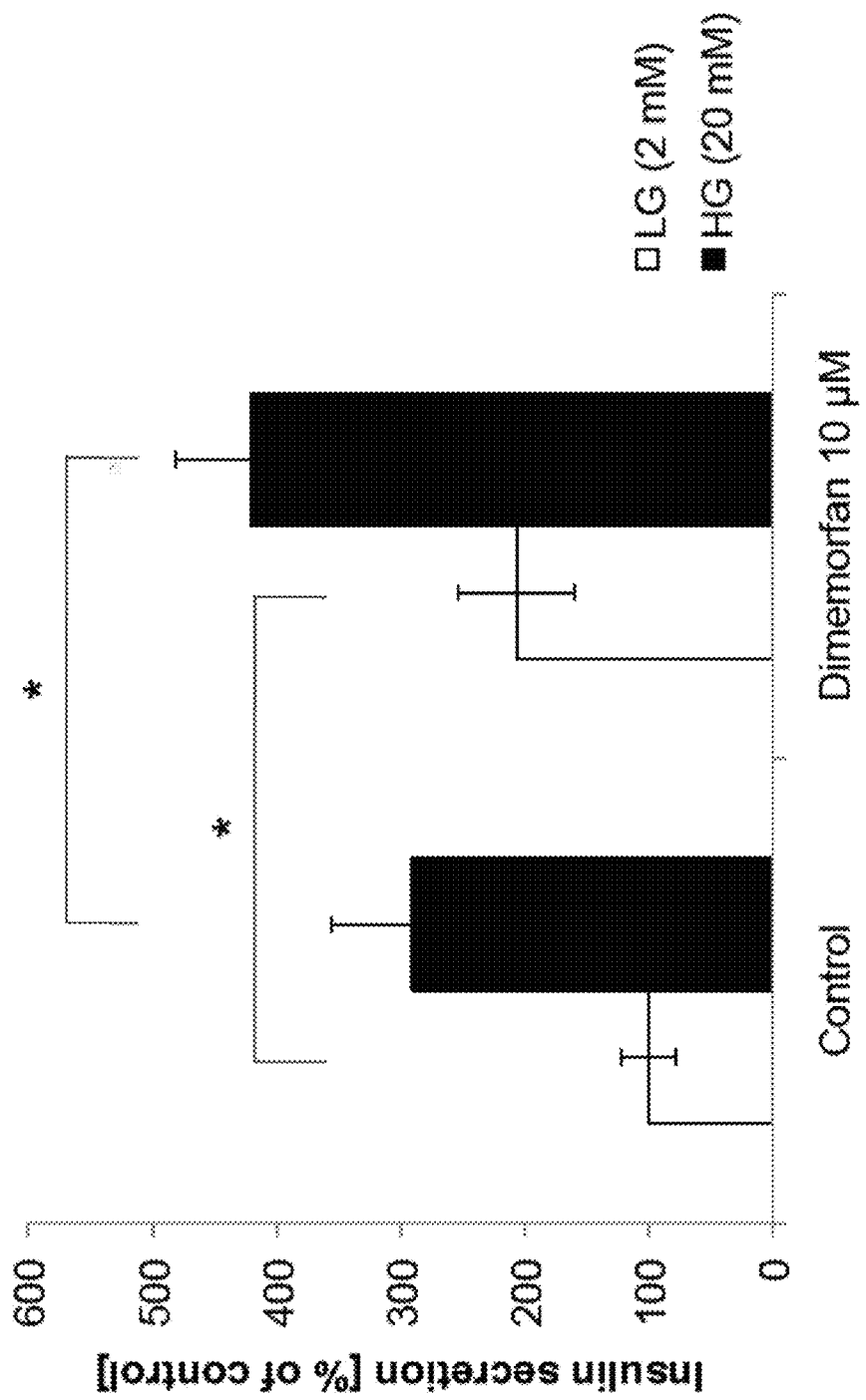
FIG. 7 shows insulin secretion from human pancreatic islets in the presence and absence of dimemorphan 10 μM. Low Glucose (2 mM); High Glucose (20 mM); the asterisks (*) indicate p values smaller than 0.05 in Student's t-tests.

FIG. 7 shows insulin secretion from human pancreatic islets in the presence and absence of dimemorphan 10 µM. Low Glucose (2 mM); High Glucose (20 mM); the asterisks (*) indicate p values smaller than 0.05 in Student's t-tests.

Example 8

Example 1 was repeated in order to compare dextrorphan, dextromethorphan, and levorphanol with one another.

Figure 8:
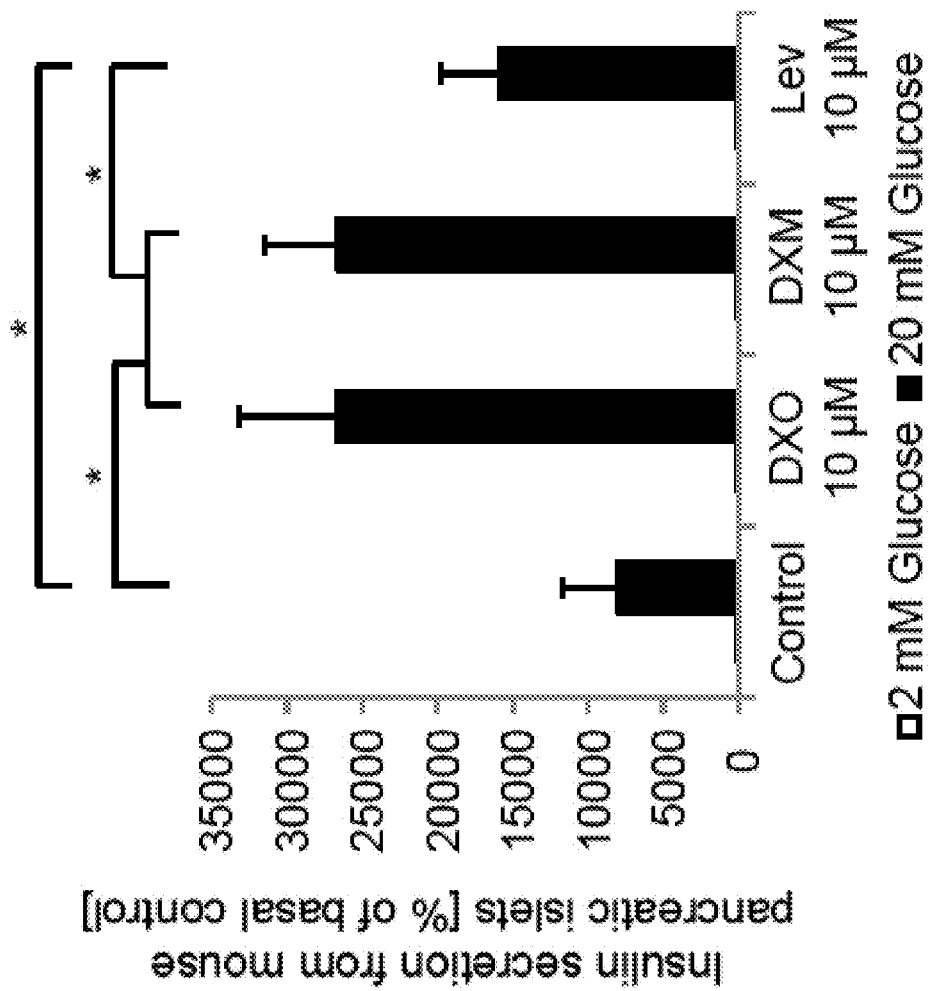
FIG. 8 shows insulin secretion from mouse pancreatic islets in the presence of dextrorphan (DXO), dextromethorphan (DXM), levorphanol (LEV), the levorotatory (−) stereoisomer of DXO that mainly targets opioid receptors rather than NMDA receptors, and a negative control; the Figure shows that DXO and DXM increase glucose-dependent insulin secretion from pancreatic islets to a significantly larger extent compared to LEV; the asterisks (*) indicate p values smaller than 0.05 in Student's t-tests.

FIG. 8 shows insulin secretion from mouse pancreatic islets in the presence of dextrorphan (DXO), dextromethorphan (DXM), levorphanol (LEV), the levorotatory (−) stereoisomer of DXO that mainly targets opioid receptors rather than NMDA receptors, and a negative control; the asterisks (*) indicate p values smaller than 0.05 in Student's t-tests.

As shown by these data, dextrorphan and dextromethorphan are significantly more effective in inducing glucose-dependent insulin secretion than levorphanol. This example illustrates that only the dextrorotatory (+) stereoisomer that targets NMDA receptors, but not the levorotatory (−) stereoisomer that mainly targets opioid receptors, increases glucose-dependent insulin secretion to a large extent and thus is useful as an efficient anti-diabetic lead compound.

Example 9

FIG. 9 shows experiments with the db/db mouse (an animal model for human type 2 diabetes mellitus). Long-term treatment with 3 mg/ml dextromethorphan (DXM) in drinking water results in significantly improved starving blood glucose levels compared to a low dose of DXM (A). In addition, the insulin content of the islets is significantly increased (B) and the beta cell area is significantly larger compared to the low dose control (C). Therefore, long-term treatment with dextromethorphan is beneficial for beta cell function and blood glucose control in a mouse model for human type 2 diabetes mellitus.

Example 10

In a clinical trial it was demonstrated that dextromethorphan (DXM) lowers blood glucose levels in male subjects with type 2 diabetes mellitus (T2DM). The study was designed as a randomized, double-blind, placebo-controlled crossover study to investigate the glucose lowering effect of oral single doses of DXM 270 mg (FIG. 10) and DXM 60 mg (FIG. 11) vs. placebo in subjects with T2DM following an oral glucose tolerance test (OGTT). DXM 270 mg, DXM 60 mg or placebo was administered orally at 0 minutes. OGTT was started at 60 minutes (75 g glucose orally). Blood glucose levels were measured at the indicated times. n=20 male with T2DM on a stable regimen of metformin monotherapy, between 45 and 70 years of age, with a BMI between 25 and 35 kg/m2, HbA1c between 7 and 8%. Student's t-test. *p=0.01, **p<0.001All values are means±SD.

Figure 10:
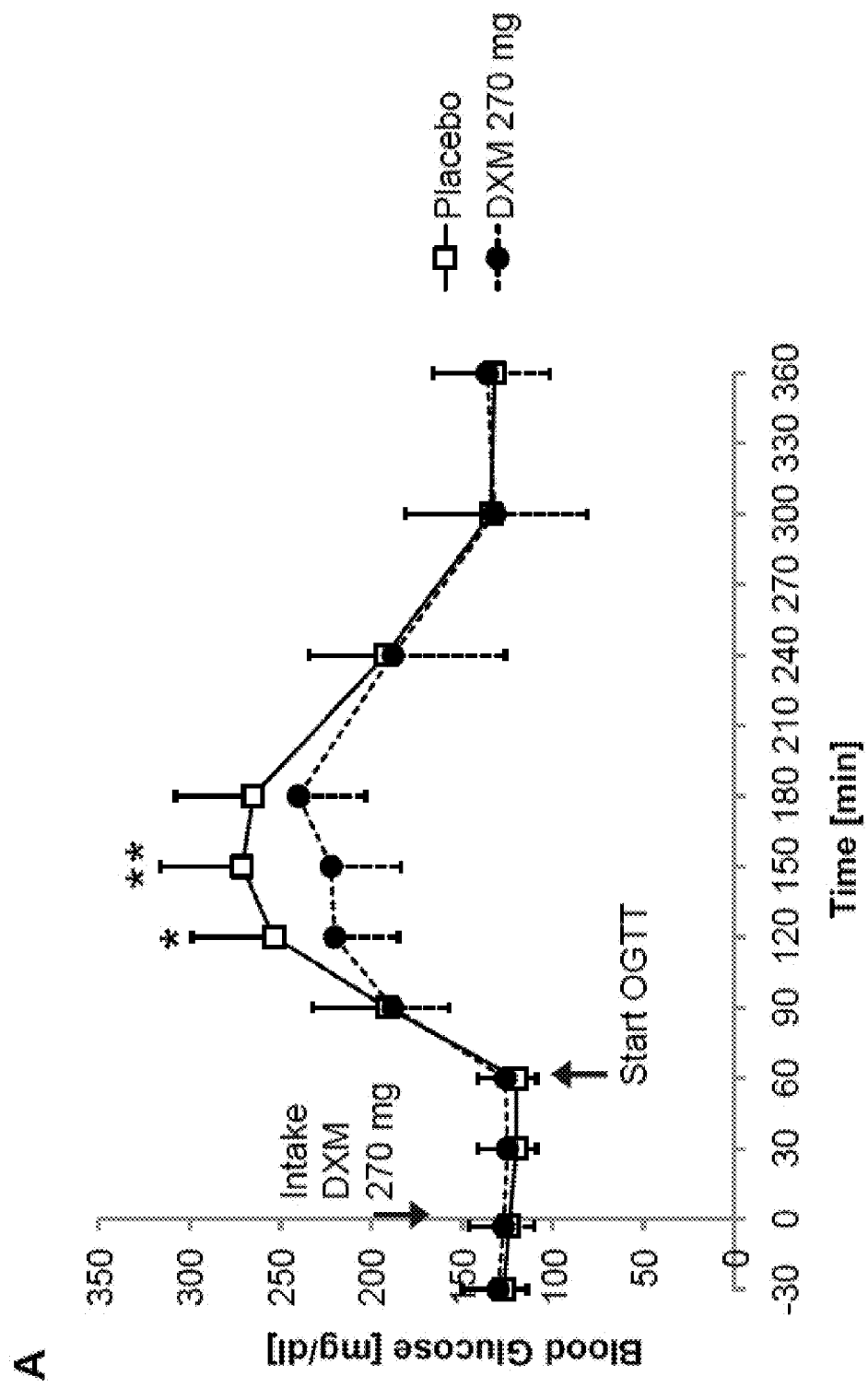
FIGS. 10 and 11 show results of a clinical trial in human subjects with type 2 diabetes designed to investigate the glucose lowering effect of oral single doses of dextromethorphan (DXM) 270 mg (FIG. 10) and 60 mg (FIG. 11) compared to placebo, respectively. The Figures show that a high dose of dextromethorphan (270 mg) significantly lowers blood glucose levels after glucose uptake in type 2 diabetic patients compared to placebo.
Figure 11:
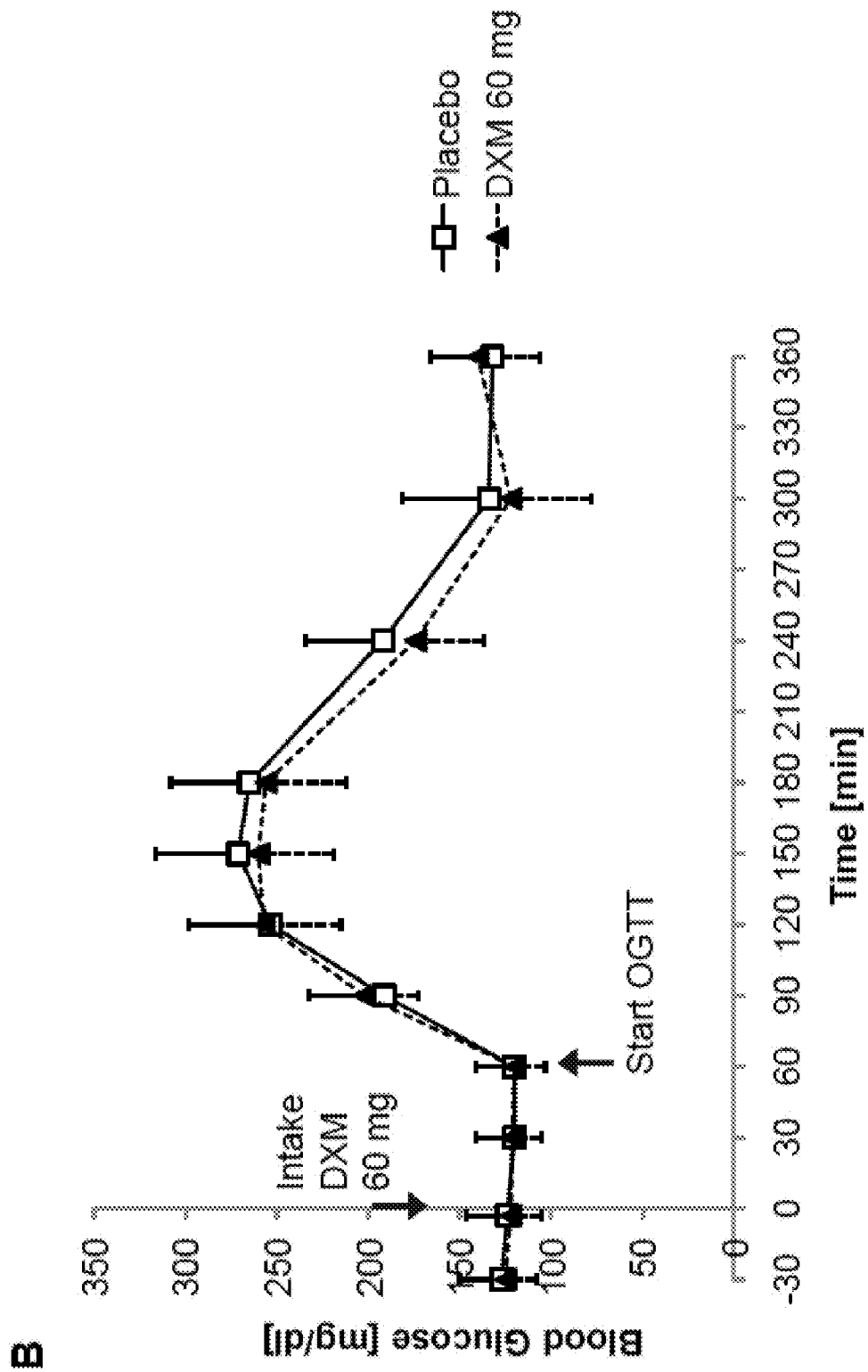

FIGS. 10 and 11 show the results for dextromethorphan (DXM) 270 mg vs. placebo (FIG. 10) and dextromethorphan (DXM) 60 mg vs. Placebo (FIG. 11).

As shown by these data, dextromethorphan 270 mg lowers significantly blood glucose levels in human subjects with type 2 diabetes during an oral glucose tolerance test, whereas dextromethorphan 60 mg is too low a concentration. Another important finding is that dextromethorphan 270 mg does not affect starving blood glucose levels and that no hypoglycemic events were observed in none of the 20 patients. The latter finding is in stark contrast to a treatment with a sulphonylurea (such as glibenclamide) that would have caused hypoglycemia in most patients during starving conditions.

Example 11

Figure 12:
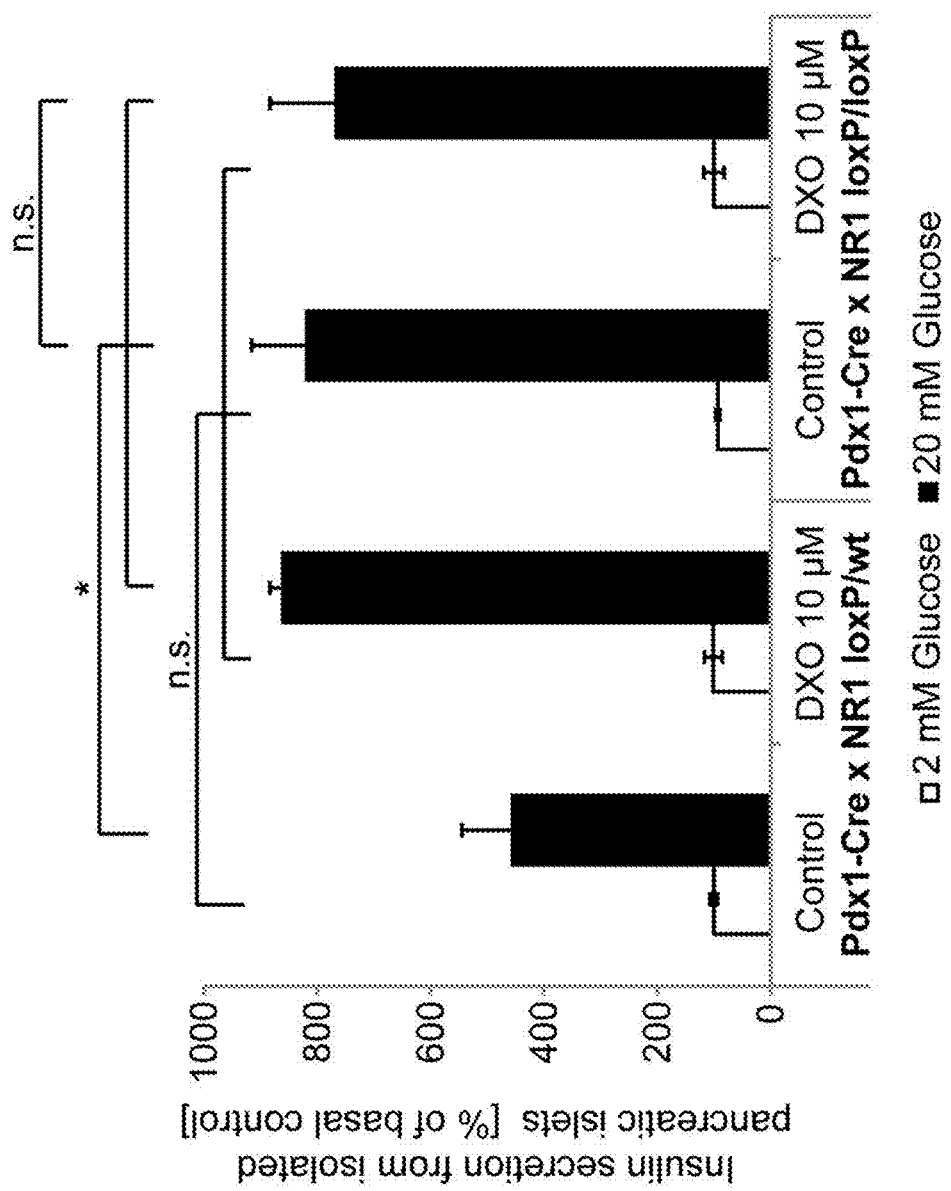
FIG. 12 shows that dextrorphan (DXO), a dextrorotatory (+)-morphinan, increases glucose-dependent insulin secretion from pancreatic islets by targeting NMDA receptors. This is because DXO cannot increase glucose-dependent insulin secretion from mouse pancreatic islets deficient for NMDA receptors (due to a homozygous deletion of the NMDA receptor subunit NR1 in mice called Pdx1-Cre×NR1 loxP/loxP) (compare last two black columns). Moreover, the effect of DXO on glucose-dependent insulin secretion is similar to the effect of a genetic deletion of NR1 in pancreatic islets. This is shown by comparing the effect of DXO on control islets harboring some NMDA receptors (called Pdx1-Cre×NR1 loxP/wt, first two black columns) to the effects of DXO on islets deficient for NMDA receptors (called Pdx1-Cre×NR1 loxP/loxP, last two black columns).

Insulin secretion from mouse pancreatic islets harboring a heterozygous deletion of the NMDA receptor-1 (Pdx1-Cre× NR1 loxP/wt=control islets) and islets harboring a homozygous deletion of NR1 (Pdx1-Cre×NR1 loxP/loxP=NR1-deficient islets) is shown in the absence or presence of 10 μM dextrorphan (FIG. 12). Low Glucose (2 mM); High Glucose (20 mM); the asterisks (*) indicate p values smaller than 0.05 in Student's t-tests; n.s., non-significant.

Deletion of NMDA receptor-1 (NR1) in pancreatic islets selectively increases glucose-dependent insulin secretion (compare first and third black column), which is similar to the effect of dextrorphan (DXO) on control islets (compare first and second black column). In addition, DXO does not further increase glucose-dependent insulin secretion when its drug target NR1 is deleted (compare third and forth column).

FIG. 12 shows that dextrorphan, a dextrorotatory (+)-morphinan, increases glucose-dependent insulin secretion by targeting NMDA receptors on pancreatic islets.

The invention claimed is:

1. A method for treating a disease or condition, using a morphinan-derivative, comprising:
   a subject seeking treatment by increasing blood insulin secretion at blood glucose concentrations elevated above normal
   administering, to the subject, an effective amount of the morphinan-derivative,
   wherein said morphinan-derivative is selected from the group consisting of
      (+)-17-methyl-(9a-13a-14a)-morphinan-3-ol (Dextrorphan), and
      (+)-3-methoxy-17-methyl-(9a-13a-14a)-morphinan (Dextromethorphan),
      or a physiologically acceptable salt including mixtures thereof in all ratios,
   where the disease or condition is selected from the group consisting of insulin-dependent diabetes mellitus, non-insulin-dependent diabetes mellitus, and/or diabetic nephropathy.

2. The method for treating a disease or condition as defined in claim 1, wherein the morphinan-derivative is provided in a pharmaceutical dosage form.

3. The method for treating a disease or condition as defined in claim 2, wherein the pharmaceutical dosage form is for oral administration.

4. The method for treating a disease or condition as defined in claim 3, wherein the pharmaceutical dosage form is selected from the group consisting of capsules, tablets, powders, granules, solutions, suspensions in aqueous or non-aqueous liquids, edible foams, foam foods, oil-in-water liquid emulsions or water-in-oil liquid emulsions.

5. The method for treating a disease or condition as defined in claim 2, wherein said subject is a human subject.

6. The method for treating a disease or condition as defined in claim 2, wherein the pharmaceutical dosage form additionally comprises metformin.

7. The method for treating a disease or condition as defined in claim 1 further comprising:
   determining that dietary management of overweight subjects and exercise alone does not result in adequate glycemic control, and
   only after said determination, administering said morphinan-derivative to said overweight subjects.

* * * * *